(12) United States Patent
Bignozzi et al.

(10) Patent No.: US 8,389,022 B2
(45) Date of Patent: *Mar. 5, 2013

(54) MATERIAL, ITEM AND PRODUCTS COMPRISING A COMPOSITION HAVING ANTI-MICROBIAL PROPERTIES

(75) Inventors: Carlo Alberto Bignozzi, Ferrara (IT); Valeria Dissette, Rovigo (IT)

(73) Assignee: NM Tech Nanomaterials Microdevice Technology Ltd. (GB)

( * ) Notice: Subject to any disclaimer, the term of this patent is extended or adjusted under 35 U.S.C. 154(b) by 726 days.

This patent is subject to a terminal disclaimer.

(21) Appl. No.: 12/445,307

(22) PCT Filed: Oct. 12, 2006

(86) PCT No.: PCT/EP2006/067361
§ 371 (c)(1),
(2), (4) Date: Oct. 14, 2009

(87) PCT Pub. No.: WO2008/043396
PCT Pub. Date: Apr. 17, 2008

(65) Prior Publication Data
US 2010/0086605 A1 Apr. 8, 2010

(51) Int. Cl.
*A61K 33/22* (2006.01)
*A61K 33/24* (2006.01)
*A61K 8/02* (2006.01)

(52) U.S. Cl. .......................... 424/657; 424/401; 424/617

(58) Field of Classification Search .................. 424/618, 424/630, 657, 641
See application file for complete search history.

(56) References Cited

U.S. PATENT DOCUMENTS

| 2005/0084464 A1 | 4/2005 | McGrath et al. |
| 2005/0249760 A1 | 11/2005 | Shin-Ching et al. |
| 2006/0141015 A1 | 6/2006 | Tessier et al. |

FOREIGN PATENT DOCUMENTS

| DE | 103 42 258 A1 | 4/2005 |
| EP | 0 937 398 A1 | 8/1999 |
| JP | 2009535326 A | 10/2009 |
| WO | WO02/085385 A2 | 10/2002 |
| WO | WO2004/073400 A2 | 9/2004 |
| WO | WO2005/042040 A1 | 5/2005 |
| WO | WO2005/042041 A1 | 5/2005 |
| WO | WO2006/049379 A1 | 5/2006 |
| WO | WO 2007/122651 A1 | 11/2007 |

OTHER PUBLICATIONS

Ludwig, C., et al, "Surface Complexation on Tio2—Part I," Journal of Colloid and Interface Science, 1995, pp. 284-290, 169, Academic Press, Inc.
Ludwig, C., et al, "Surface Complexation on Tio2—Part II," Journal of Colloid and Interface Science, 1995, pp. 291-299, 169, Academic Press, Inc.
Schläpfer, C.W., et al, "The Structure and Properties of Tio2-Cu(II)-EDTA Ternary Surface Complexes," Journal of Colloid and Interface Science, 2001, pp. 200-208, 239, Academic Press.

*Primary Examiner* — Gina C Justice
(74) *Attorney, Agent, or Firm* — Laubscher & Laubscher, P.C.

(57) ABSTRACT

A coating product composition has the general formula $AO_x\text{-}(L\text{-}Me^{n+})_i$, wherein $AO_x$ is a metal or metalloid oxide in which x indicates the number of the Oxygen atom(s) (O) bonded to the metal (A) atom, $Me^{n+}$ is a metal ion, L is a bifunctional molecule that could bind both metal oxide or metalloid oxide $(AO_x)$ and the metal ion $(Me^{n+})$, i is the number of the $(L\text{-}Me^{n+})$ groups bound to the metal oxide $AO_x$. The value of the parameter i depends on various factors, such as the size of the nanoparticle of $AO_x$, and the nature of the molecule L.

15 Claims, 1 Drawing Sheet

MATERIAL, ITEM AND PRODUCTS COMPRISING A COMPOSITION HAVING ANTI-MICROBIAL PROPERTIES

This application is a National Stage Application under 35 U.S.C. §371 of PCT International Application No. PCT/EP2006/067361 filed on Oct. 12, 2006. The entire contents of PCT/EP2006/067361 is incorporated herein by reference.

The invention relates to nanomaterials, nanomaterial products, material and items comprising nanomaterial composition, such as for example plastics, fabrics, tissues and paints.

Moreover, the invention relates to nanomaterials, nanomaterial products, material and items comprising a nanomaterial composition having antibacterial, antimicrobial, antiviral, antimycotic, germicide, photo-remediating properties.

Furthermore, the invention relates to a product for topical use having antibacterial, antimicrobial, antiviral, antimycotic, germicide properties.

Contagious diseases spread very fast and in a very simple manner between users of public buildings such as schools, swimming pools, theatres, gymnasiums, or also buses, trains, thus giving rise to epidemic diseases.

It is, therefore, very important to avoid the proliferation of bacteria, or fungi, or other microorganisms, so as to avoid spreading infections or other diseases to the different users of such facilities.

Moreover, for certain types of person the contagion could be very dangerous, for example for newborn babies, or old persons, or patients in hospitals.

It is, thus, necessary to provide in public facilities conditions that prevent contagion between the different users of the public facility.

It is, furthermore, necessary to provide wall, and/or floor, and/or furniture coatings, allowing preventing the spreading of infections.

Furthermore, it is very important to restore hygienic conditions, if necessary, and to maintain such hygienic conditions in public facilities.

Sometimes, it is very difficult, or also almost impossible to effectively restore hygienic conditions in public facilities both because of the complexity of sanitization methods that sometimes require the evacuation of the public facility, and because of the ineffectiveness of the sanitization methods.

It is also important that each surface, or zone of public facilities has hygienic conditions to prevent non-hygienic zones or surfaces acting as centres for bacteria proliferation that in turn would spread within very short period of time in almost all the public facility.

Furthermore, air-conditioning systems could contribute to spreading infections to all the users of a public facility by circulating the air.

Furthermore, in some industries, for example in the food industry, it is necessary to avoid bacteria proliferation in order to maintain hygienic conditions into the products processed into the industry, for example a food product.

In farms, and in slaughterhouses, bacteria proliferations are, on the one hand very common, and on the other hand it is very important to limit and avoid such proliferations. In agriculture, it is often necessary to treat plants, or fruit trees, or vegetables, or also flowers, with specific products to eliminate bacteria, or fungi or other microorganisms, and to avoid a proliferation thereof that would adversely affect the quality of the vegetables or of the fruit, or would compromise the entire harvest of the farmer.

Moreover, it is necessary to use on the one hand a product that is efficacious against the specific bacteria, and possibly against many different bacteria, or microorganisms, and on the other hand to use a product that is non-polluting both for the environment and for the fruit or vegetable treated with the product.

Known products are often inefficacious against many microorganisms, therefore many different products have to be used, and also known products are often polluting both for the environment and for the product for which they are used.

Moreover, it is necessary to clean thoroughly public buildings, or industries, or hospitals, slaughterhouses for removing bacteria, but known detergents are often inefficacious in removing all the bacteria present in such facilities.

Moreover, when possible contagion is suspected, a person has to wash himself to remove bacteria, or other infective microorganisms, this necessity arises, for example, for doctors or those working in hospitals.

Moreover, in order to prevent any subsequent bacteria growth and/or proliferation the necessity arises to produce antibacterial materials that also maintain this property over time.

It is also important, for such a material to have an almost homogeneous structure so that no bacteria proliferation centre can develop into the structure of such a material.

Moreover, certain diseases, mainly cutaneous diseases, are very widespread and although not fatal, such diseases are however unpleasant for the persons affected thereby.

For example, acne is very widespread, mostly among adolescents, and adolescents affected by acne often feel very uneasy and have problems relating to others.

Moreover, it is very difficult to treat acne so as to make the pustules disappear from the skin of a person affected by acne, and most of all make the pustules disappear without leaving any scares.

Known products are not very efficacious, and the pustules due to the acne remain on the skin of the affected person for a very long period of time, and also the acne contagion may also spread to other zones of the skin that were previously not affected by acne.

Furthermore, known products do not allow scars due to acne to be avoided.

Such scars are unsightly, also the scars are mainly on the skin of the face and therefore may not be hidden with clothes or scarves, and have to be thermally treated to be eliminated.

Therefore such scares cause many problems mainly for relations with other persons. Similar problems may arise for a person affected by Herpes virus.

Such virus creates painful and unsightly vesicles, particularly in the skin of a face of a person.

Such vesicles may create many problems for the relationships of a person affected thereby.

Moreover, since the vesicles are caused by a virus, it is very important to avoid any contagion by the virus of other zones of the skin of an affected person previously free of vesicles, and also to avoid any contagion of other persons.

Also in case of burns or other irritations, or inflammations of the skin, or also in the case of excoriations, or abrasions, or ulcers, such as decubitus ulcers, it is important to provide a topical product that can be applied to the affected area of the skin for efficaciously treating the disease of the affected area.

Often, known products are inefficacious for treating such diseases, and/or require a very long application time for showing the first results of treating the skin affection, and/or are too aggressive for the skin of a patient.

Moreover, often on the affected skin infections grow up due to external microbes.

The ulcers, excoriations, etc. may be infected by external microbes and the recovery becomes slower and very strong medicine have to be taken in order to try treating the infection.

The need thus arises to provide a new product for topical use that is efficacious in treating the aforementioned cutaneous affections, and that on the other has a good cutaneous tolerance, and that may form an efficacious barrier against external microbes, so avoiding any infection on the affected skin.

Moreover a cicatrizing product is often required that has a good cutaneous compatibility and is also efficacious in cicatrizing the skin and avoiding any external contagion to the wound to be cicatrized.

Furthermore, many persons, suffer because they smell of sweat and/or because have body odour, and have many problems in relationships with other persons.

US2005/0249760 discloses a repair gel for the human body which contains photocatalist TiO2 particles coated with nanosilver coating to produce nano TiO2Ag compound. US2005/0084464 discloses a method for reducing odor using metal-modified particles. The method uses a chelating agent to attach transition metals to nanoparticles comprising various materials such as silica or other oxides. The chelating agent helps to bond the metal to the nanoparticles.

The need thus arises for a deodorizing product that is efficacious in deodorizing, that has a good cutaneous tolerance, and that is also efficacious against the microbes responsible for the bad body odour.

An object of the invention is to improve known coatings, such as for example, tiles, panels, carpeting, rugs, and linoleum coatings, known furniture, known materials.

Another object is to provide coatings, such as for example, tiles, panels, carpeting, rugs, linoleum coatings, furniture, materials, having antibacterial, antimycotic, antiviral, anti-pollution, self-cleaning properties.

Still another object is to improve known cleansing products.

Another object is to provide cleansing products having antibacterial, antimycotic, antiviral properties.

Still another object is to improve known painting products.

A further object is to provide a painting product having antibacterial, antimycotic, antiviral, anti-pollution, self-cleaning properties.

A further object is to improve the properties of known items.

Still further object is to provide items having antibacterial, antimycotic, antiviral, anti-pollution, self-cleaning properties.

Still further object, is to provide a filter, in particular to be used in air-conditioning systems, having antibacterial, antimycotic, antiviral, anti-pollution, self-cleaning properties.

Another object is to provide surgical instruments having antibacterial, antimycotic, antiviral properties.

Still another object is to provide sanitary napkin and/or linen having antibacterial, antimycotic, antiviral properties.

A further object is to improve a known topical-treatment product, such as a cream, a gel, or a powder for topical use.

Another object is to provide a topical-treatment product having antibacterial, antimycotic, antiviral properties.

Still another object is to provide a topical-treatment product for treating acne diseases.

Still another object is to provide a topical-treatment product for treating herpes diseases.

Still another object is to provide a topical-treatment product for treating skin ulcers, and in particular bedsores, or decubitus ulcers.

A further object is to provide a topical-treatment product for treating cutaneous irritations, and/or inflammations, and/or abrasions, and/or excoriations, and/or burns.

A further object is to provide a topical cicatrizing product for cicatrizing the skin of a user thereof.

Another object is to provide a lenitive topical-treatment product for relieving topical affections.

A further object is to provide a deodorizing product for topical use for deodorizing the skin of a user.

According to a first aspect of the invention, there is provided a coating product comprising a composition having the general formula $AO_x\text{-}(L\text{-}Me^{n+})_i$, wherein L is a molecule comprising at least a first functional group bonded to said metal oxide $AO_x$, and at least a second functional group bonded to said ion $Me^+$, said first functional group comprising boronic ($-B(OH)_2$), and/or phosphonic ($-PO_3H_2$) functionality.

According to a second aspect of the invention, there is provided a method for obtaining coatings comprising adding a coating product with a composition having the general formula $AO_x\text{-}(L\text{-}Me^{n+})_i$, wherein L is a molecule comprising at least a first functional group bonded to said metal oxide $AO_x$, and at least a second functional group bonded to said ion $Me^+$, said first functional group comprising boronic ($-B(OH)_2$), and/or phosphonic ($-PO_3H_2$) functionality.

According to a third aspect of the invention, there is provided the use of a coating product comprising a composition having the general formula $AO_x\text{-}(L\text{-}Me^{n+})_i$ for reclaiming a surface, wherein L is a molecule comprising at least a first functional group bonded to said metal oxide $AO_x$, and at least a second functional group bonded to said ion $Me^+$, said first functional group comprising boronic ($-B(OH)_2$), and/or phosphonic ($-PO_3H_2$) functionality. $AO_x$ is a metal or metalloid oxide in which x indicates the number of the Oxygen atom(s) (O) bound to the metal (A) atom; $Me^{n+}$ is a metal ion, having antibacterial, antiviral, antimycotic activity; L is a bifunctional molecule that could bind both metal oxide or metalloid oxide ($AO_x$) and the metal ion ($Me^{n+}$), and i is the number of ($L\text{-}Me^{n+}$) groups bound to the metal oxide $AO_x$, and the value of the parameter i depends on various factors, such as the size of the nanoparticle of $AO_x$, the nature of the molecule L.

Owing to these aspects of the invention it is possible to remove bacteria, or other undesired and/or dangerous microorganisms from a surface only by applying such a coating product to the desired surface, so obtaining a hygienic surface, and conferring such properties to the treated surface.

It is also possible to remove pollution, both organic, and inorganic, from a surface only by applying such a coating product to the desired surface.

A self-cleaning surface can also be obtained.

Moreover, such a coating product maintains antibacterial, antiviral, antimycotic properties over time, avoiding any subsequent bacteria proliferation on the treated surface.

Therefore a surface can be obtained, for example a wall of a building, of a room, that maintains over time the antibacterial, antiviral, antimycotic properties.

The need for subsequent treatments for reclaiming antibacterial properties is therefore avoided.

Such coating product maintains also self-cleaning properties; therefore, it is possible to obtain a self-cleaning surface, avoiding the necessity of subsequent treatments for removing pollution therefrom.

Further, in case of necessity, it is possible to restore the properties of the coating product, in case for example of depletion of the metal ion(s), for example by wetting such a coating product with an alcoholic solution containing the same metal ion(s) present into the composition having the general formula $AO_x\text{-}(L\text{-}Me^{n+})_i$.

Bacteria proliferation and spreading of infections are avoided on surfaces treated with such a coating product.

Moreover, the very limited particle size of the composition having the general formula $AO_x\text{-}(L\text{-}Me^{n+})_i$, allow finely disperse such composition into the structure of the coating product, and therefore a coating product having homogeneous properties can be obtained.

Moreover, with such a coating product can be obtained homogeneous film that would homogeneously cover a surface on which such coating product is applied.

Therefore, on surface treated with such a coating product possible bacteria proliferation or growth centre cannot be found.

Furthermore, metal or metalloid oxide $AO_x$ adhere to any different suitable substrate, and in case, by further adding a particular additive to the coating product, it is possible to obtain a coating product that can be suitably applied to several different substrates, such as for example wood, plastic, glass, metals, ceramics, cement, and internal and external building surfaces.

Further, such coating product has antibacterial, anti-pollution activity also in absence of solar light, or of any other light source, and can therefore be applied to any desired substrate assuring hygienic conditions thereof.

In case, before applying such a coating product to the desired surface, a primer can be applied on the surface so as to enhance the adhesion of the coating product and to protect the surface.

In a version, the coating product can comprise a painting product.

In this case a pigment, and/or a binder, and/or a filler, and/or a diluting element, and/or an additive, may be mixed to the painting product for obtaining a painting product having the desired features, such as for example, density, colour, consistency, etc., and for obtaining a paint substrate having the desired propertied such as for thickness, colour, brightness, or opacity, etc.

Moreover, the composition $AO_x\text{-}(L\text{-}Me^{n+})_i$ can be used for obtaining suspensions either in aqueous or in other solvents, for example polar solvents, therefore different kind of a coating products suitable for being applied to different kind of surfaces can be obtained.

For example, such a coating product can be used for coating plastics, ceramics, synthetic materials, natural rubber, synthetic rubber, wood, natural stone, marble, metal, aluminium, iron, glass, cement, linoleum, textiles, carpeting, rugs, etc., provided with antibacterial, antimicrobial, anti-pollution, properties.

It is also possible to obtain an anti-pollution coating product allowing organic and inorganic pollution to be removed form a surface on which such coating product is applied, and/or from a medium contacting such coating product, and avoiding any pollution, or dirty deposition thereon.

By suitably choosing the solvent of the coating product, it is also possible to obtain transparent coating product that could be applied on to a desired surface without altering the aesthetical appearance thereof.

Therefore such a coating product could be applied for example, on statues, aesthetical creations, external surface of building that are located outside, and, therefore subjected to air pollution.

Further, by adding a desired pigment it is possible to obtain a coloured coating product.

Further, suspensions of the composition $AO_x\text{-}(L\text{-}Me^+)$, are stable over time, and therefore coating products that are stable over time can be obtained, avoiding the need to mix the components of the coating product only just before applying such coating product.

Moreover by adding a suitable pigment a stain can be obtained, that can be subsequently in turn used for obtaining a painting product.

It is also possible to obtain material provided with a coating product conferring to said material antibacterial, antiviral, antimycotic, self-cleaning, photocatalytic, anti-mildew properties.

Since the coating product according to the invention may be applied on to any desired materials, a very wide range of material with such properties may be obtained.

According to a fourth aspect of the invention, there is provided a product comprising a base material and a composition having the general formula $AO_x\text{-}(L\text{-}Me^{n+})_i$.

According to a fifth aspect of the invention, there is provided a method for producing a material wherein coating said material with a coating product comprising a composition having the general formula $AO_x\text{-}(L\text{-}Me^{n+})_i$ it is provided for.

According to a seventh aspect of the invention, there is provided a method for producing a product comprising mixing with a base material of said product a composition having the general formula $AO_x\text{-}(L\text{-}Me^{n+})_i$.

According to these aspects of the invention, it is possible to obtain materials and products provided with antibacterial, antiviral, antimicrobial, photocatalytic properties, that can be thus used for obtaining items with the aforementioned properties.

Self-cleaning materials and products can further be obtained.

A composition having the general formula $AO_x\text{-}(L\text{-}Me^{n+})_i$ is suitable for being applied to, or mixed with, in case diluted with suitable solvents, any desired materials, therefore many different materials and products with antibacterial properties can be obtained.

For example, such a composition can be used for obtaining plastics, ceramics, synthetic materials, natural rubber, synthetic rubber, wood, natural stone, marble, metal, aluminium, iron, glass, cement, linoleum, textiles.

Furthermore, materials with very homogeneous properties can be obtained.

Such a composition may be mixed to a base material in flowable state obtaining a product having the aforementioned properties.

Such a composition can further be mixed with a desired base material during the preparation process of a product, for example can be added to melt plastics, or glass intimately mixing with the structure of the plastics.

It is possible to obtain plastics, or glass material having a very homogeneous structure, in which structure the composition having the general formula $AO_x\text{-}(L\text{-}Me^{n+})_i$ is very homogeneously mixed, and therefore antibacterial properties are homogeneously present in such materials.

Materials and products obtained have no bacteria proliferation centre and have very high hygienic conditions.

Such materials can be used for making objects, items, coatings provided with antibacterial properties.

According to an eighth aspect of the invention, a cleansing product is provided comprising a composition having the general formula $AO_x\text{-}(L\text{-}Me^{n+})_i$.

According to a ninth aspect of the invention, a method is provided for preparing a cleansing element comprising adding a cleansing product with a composition having the general formula $AO_x\text{-}(L\text{-}Me^{n+})_i$.

According to these aspects of the invention, it is possible to obtain a cleansing product having antibacterial, antimicrobial, antiviral, antimycotic, anti-pollution properties that can be used for cleaning a desired surface, reclaiming hygienic properties thereof.

Such a cleansing product can be used for example for cleaning floors, or walls in hospitals, schools or other public facilities, for cleaning bathrooms, public baths, showers, so avoiding bacteria proliferation.

A cleansing product efficacious against many microorganisms such as for example: HSV-1 (Herpes Simplex Virus-1), Adenovirus, Poliovirus, Aviaria virus, *Legionella pneumophila, Pseudomonas aeruginosa, Staphilococcus aureus, Enterococcus faecalis, Escherica Coli, Salmonella enteridis D1, Listeria monocytogenes, Candida albicans, Aspergillus niger*, may be obtained.

In a version, said cleansing product comprises a surfactant for improving the removal of dirty, and/or an abrasive agent for improving the removal of dirty, and/or pH modifier for improve the efficacy of the cleansing, and/or a water softener for counteracting the hardness of the water, an oxidant for bleaching, a non-surfactant for keeping dirty in suspension, enzyme for digesting proteins, fats, or carbohydrates in dirty, or for modifying fabric fel, a foaming modifier, an optical brightener, and/or a colour, and/or a perfume, and/or an essence for improving the removal of dirty, or the efficacy and the performances of the cleansing product.

By further adding further suitable additives a cleansing product suitable for cleaning skin or hair, can be obtained. In a version, the cleansing product further comprises sodium laureth sulfate, and/or glycol distearate, and/or natural oil, and/or coconut oil, and/or inseed oil, and/or tocopherol, and/or pantothetic acid.

Such a cleansing product would remove dirty from the skin or hair, and also would remove bacteria thereof, so avoiding proliferation of certain diseases.

According to a tenth aspect of the invention a sterilising product is provided comprising a composition having the general formula $AO_x$-$(L-Me^{n+})_i$.

According to a eleventh aspect of the invention a method for preparing a sterilising product comprising adding a composition having the general formula $AO_x$-$(L-Me^{n+})_i$ there is provided for.

According to a twelfth aspect of the invention, a method is provided for sterilising object comprising bringing said object into contact with a sterilising product comprising a composition having the general formula $AO_x$-$(L-Me^{n+})_i$.

According a thirteenth aspect of the invention, a method is provided for sterilising surgical instruments comprising bringing said surgical instruments into contact with a sterilising product comprising a composition having the general formula $AO_x$-$(L-Me^{n+})_i$.

According to a fourteenth aspect of the invention there is provided a method for obtaining surgical instruments comprising at least partly coating said surgical instruments with a coating product with a composition having the general formula $AO_x$-$(L-Me^{n+})_i$.

Owing to these aspects, it is possible to obtain surgical instruments that maintain antibacterial, antiviral, properties over time and that do not need to be deep sterilised between two different uses.

It is also possible to obtain a very efficacious sterilising product.

According to a fifteenth aspect of the invention, a biocide product is provided comprising a composition having the general formula $AO_x$-$(L-Me^{n+})_i$.

According to a sixteenth aspect of the invention, a method is provided for preparing biocides comprises adding a biocide product with a composition having the general formula $AO_x$-$(L-Me^{n+})_i$.

According to a seventeenth aspect of the invention, the use of a biocide product comprising a composition having the general formula $AO_x$-$(L-Me^{n+})_i$, there is provided for.

Owing to these aspects of the invention, it is possible to obtain a biocide product that is efficacious for removing several different organisms, such as bacteria, fungi, sponges, and mildews.

It is also possible, to obtain a biocide product that could be spread on the desired surface either by spraying, or be applied to the desired surface.

It is also possible, to obtain a non-polluting biocide that could cover almost homogeneously the surface to which it is applied, therefore removing almost completely any bacteria or microorganisms present on such surface, and avoiding almost completely any subsequent proliferation thereof.

It is also possible to obtain a biocide product that is very efficacious for removing bacteria as, for example *Pseudomonas, Erwinia amilovora, Xanthomonas campestris*, fungi, from plants, flowers, trees.

It also possible to obtain a non-pollution biocide product that can be used in agriculture without any limitation due to the environmental laws.

According to an eighteenth aspect of the invention, a prosthesis product is provided comprising a composition having the general formula $AO_x$-$(L-Me^{n+})_i$.

According to a nineteenth aspect of the invention, there is provided a method for preparing a prosthesis element comprising at least partly coating said prosthesis element with a coating product comprising a composition having the general formula $AO_x$-$(L-Me^{n+})_i$.

According to a twentieth aspect of the invention, there is provided a method for preparing a prosthesis element comprising mixing prosthesis material with a product comprising a composition having the general formula $AO_x$-$(L-Me^{n+})_i$.

Owing to these aspects of the invention, it is possible to obtain a prosthesis element that avoid any bacteria proliferation, and therefore infections to the patient.

Rejection phenomena would be also limited or avoided, and therefore further troubles to the patient, due for example to a subsequent implantation of a new prosthesis, may be avoided.

According to a twenty-first aspect of the invention, there is provided a filter provided with a coating product comprising a composition having the general formula $AO_x$-$(L-Me^{n+})_i$.

According to a twenty-third aspect of the invention, there is provided a method for preparing a filter comprising at least partly coating said filter with a coating product comprising a composition having the general formula $AO_x$-$(L-Me^{n+})_i$.

Owing to these aspects of the invention, it is possible to obtain filtering systems, such as for example air-conditioning systems that would do not contribute to spreading infections, but remove any bacteria or other microorganisms, or pollution from the air circulating therein.

Air-circulating systems improving the quality of the air in a room or in a building can thus be obtained.

According to a twenty-fourth aspect of the invention, there is provided a method for preparing a sanitary napkin comprising mixing a product having the general formula $AO_x$-$(L-Me^{n+})_i$ to absorbent material of said sanitary napkin.

According to a twenty-fifth aspect of the invention, there is provided a method for obtaining a sanitary napkin comprising applying a product having the general formula $AO_x$-$(L-Me^{n+})_i$ to said sanitary napkin.

According to a twenty-sixth aspect of the invention, there is provided a sanitary napkin product comprising a composition having the general formula $AO_x\text{-}(L\text{-}Me^{n+})_i$.

According to a twenty-seventh aspect of the invention, there is provided a method for sanitizing a sanitary napkin comprising bringing said sanitary napkin into contact with a product having the general formula $AO_x\text{-}(L\text{-}Me^{n+})_i$.

According to a twenty-eighth aspect of the invention, there is provided a method for sanitizing linen comprising bringing said linen into contact with a product having the general formula $AO_x\text{-}(L\text{-}Me^{n+})_i$.

Owing to these aspects of the invention, it is possible to obtain antibacterial sanitary napkin and linen avoiding any proliferation of bacteria, fungi, virus, thereon.

It is also possible to avoid any bacteria proliferation in dustbins, or containers, into which dirty sanitary napkin are collected.

This is particularly important in certain facilities where there are many users, for example, hospitals, or hospices, between whom different diseases could spread.

It is possible to avoid any bacteria proliferation in linen baskets, or containers in which dirty linen, such as bed linen, or towels, are collected before being washed.

This is particularly important in certain facilities for example, hospitals, or hospices where there are many users, between whom different diseases could spread.

According to a twenty-ninth aspect there is provided the use of a composition with the general formula $AO_x\text{-}(L\text{-}Me^{n+})_i$ for obtaining a topical-treatment product for treating acne diseases.

According to a thirtieth aspect of the invention, there is provided the use of a composition having the general formula $AO_x\text{-}(L\text{-}Me^{n+})_i$ for a obtaining topical-treatment product for treating herpes diseases.

According to a thirty-first aspect of the invention, there is provided the use of a composition having the general formula $AO_x\text{-}(L\text{-}Me^{n+})_i$ for a obtaining topical-treatment product for treating skin ulcers, and in particular decubitus ulcers.

According to a thirty-second aspect of the invention, there is provided the use of composition a having the general formula $AO_x\text{-}(L\text{-}Me^{n+})_i$ for obtaining a topical-treatment product for treating skin irritations, and/or skin inflammations, and/or skin abrasions, and/or skin excoriations.

According to a thirty-third aspect of the invention, there is provided the use of a composition having the general formula $AO_x\text{-}(L\text{-}Me^{n+})_i$ for obtaining a lenitive topical-treatment product.

According to a thirty-fourth aspect of the invention, there is provided the use of a composition having the general formula $AO_x\text{-}(L\text{-}Me^{n+})_i$ for obtaining a cicatrizing topical-treatment product for cicatrizing the skin of a user of said cicatrizing product.

According to a thirty-fifth aspect of the invention, there is provided the use of a composition having the general formula $AO_x\text{-}(L\text{-}Me^{n+})_i$ for obtaining a burn topical-treatment product for treating burns on the skin of a user of said topical-treatment product. By suitably choosing the compounds in the composition having the general formula $AO_x\text{-}(L\text{-}Me^{n+})_i$ topical-treatment products efficacious against many different diseases may be obtained, moreover, topical-treatment products having antiviral, antibacterial, antimicrobial, antimycotic may be obtained.

According to a thirty-sixth aspect of the invention, there is provided the use of a composition having the general formula $AO_x\text{-}(L\text{-}Me^{n+})_i$ for obtaining a topical-treatment product for treating diseases due at least by one of the following microbes: HSV-1 (Herpes Simplex Virus-1), Adenovirus, Poliovirus, Aviaria virus, *Legionella pneumophila, Pseudomonas aeruginosa, Staphilococcus aureus, Enterococcus faecalis, Escherica Coli, Salmonella enteridis* D1, *Listeria monocytogenes, Candida albicans, Aspergillus niger*.

For example the composition having the general formula $AO_x\text{-}(L\text{-}Me^{n+})_i$ further comprises a quaternary ammonium salt for enhancing the antiviral, antibacterial, antimicrobial, antimycotic properties of the topical-treatment product.

According to a thirty-seventh aspect of the invention, there is provided a method for obtaining a topical-treatment product for treating acne diseases comprising adding a composition having the general formula $AO_x\text{-}(L\text{-}Me^{n+})_i$.

According to a thirty-eighth aspect of the invention, there is provided a method for obtaining a topical-treatment product for treating herpes diseases comprising adding a composition having the general formula $AO_x\text{-}(L\text{-}Me^{n+})_i$.

According to a thirty-ninth aspect of the invention, there is provided a method for obtaining a topical-treatment product for treating skin ulcers, and in particular decubitus ulcers, comprising adding a composition having the general formula $AO_x\text{-}(L\text{-}Me^{n+})_i$.

By suitably choosing the compounds in the product having the general formula $AO_x\text{-}(L\text{-}Me^{n+})_i$ topical-treatment products efficacious against many different diseases may be obtained, moreover topical-treatment products having antiviral, antibacterial, antimicrobial, antimycotic properties may be obtained.

According to a fortieth aspect of the invention, there is provided a method for a obtaining topical-treatment product for treating diseases due at least by one of the following microbes: HSV-1 (Herpes Simplex Virus-1), Adenovirus, Poliovirus, Aviaria virus, *Legionella pneumophila, Pseudomonas aeruginosa, Staphilococcus aureus, Enterococcus faecalis, Escherica Coli, Salmonella enteridis* D1, *Listeria monocytogenes, Candida albicans, Aspergillus niger*, comprising adding a composition having the general formula $AO_x\text{-}(L\text{-}Me^{n+})_i$.

The composition having the general formula $AO_x\text{-}(L\text{-}Me^{n+})_i$ may be added to any known topical-treatment products to thus obtain topical-treatment products for example in form of cream, or gel, or powder, means having antibacterial, antimicotic, virucidal, antimicrobial properties.

For example such composition may be added to a common daily, or night cream, or to a moisturizing cream, thus conferring the aforementioned properties thereupon.

Owing to these aspects of the invention, it is possible to obtain topical-treatment products having antiviral, antibacterial, antimicrobial, antimycotic properties, together with other curative properties.

Therefore very efficacious topical-treatment products may be obtained.

In fact, the antiviral, antibacterial, antimicrobial, antimycotic properties allow the curative properties of the topical-treatment products to be enhanced since any microbial proliferation growth is avoided, and any spread of the contagion to different areas of the skin is also avoided, and also any external contagion is also avoided.

Therefore, any infection of the skin is avoided and the curative process is more efficacious and faster than usual.

Therefore very curative topical-treatment products efficacious for example against burns, irritations, inflammations, excoriations, and abrasions of the skin of a user may be obtained.

The topical-treatment product comprises for example a cream, a gel, and/or a powder.

Moreover, by suitably choosing the elements in the composition having the general formula $AO_x\text{-}(L\text{-}Me^{n+})_i$ may be obtained a product compatible and thus mixable with any physical form of the cream, for example emulsions, gels, suspensions, foams, microbeadlets, microspheres, granules, microgranules, multiple emulsions, e.g. water-in-oil-in-water emulsions.

Owing to the composition and the dimensions of the composition having the general formula $AO_x\text{-}(L\text{-}Me^{n+})_i$, very homogeneous topical-treatment products may be further obtained.

Moreover adding the composition having the general formula $AO_x\text{-}(L\text{-}Me^{n+})_i$ does not require further additional step or particular precautions in the known processes for preparing topical-treatment products.

Therefore, by simply further providing the adding phase for adding the composition having the general formula $AO_x\text{-}(L\text{-}Me^{n+})_i$ known processes for producing topical-treatment products may be modified in order to produce topical-treatment products having antibacterial, antimicrobial, antimycotic, virucidal properties.

According to a forty-first aspect of the invention, it is provided a deodorizing product comprising a composition having the general formula $AO_x\text{-}(L\text{-}Me^{n+})_i$.

In a version said deodorizing product is in powder form.

In a further version said deodorizing product is in spray, and/or cream form, and/or gel form, and/or aerosol form.

Owing to the very limited dimension of the composition having the general formula $AO_x\text{-}(L\text{-}Me^{n+})_i$, deodorizing product having very homogeneous properties may be obtained.

According to a forty-second aspect of the invention, it is provided the use of a composition having the general formula $AO_x\text{-}(L\text{-}Me^{n+})_i$ for obtaining a deodorizing product.

Owing to the properties of the composition having the general formula $AO_x\text{-}(L\text{-}Me^{n+})_i$ it is possible to obtain very efficacious deodorizing products, and also deodorizing products having antibacterial, antimicrobial, antimycotic, virucidal properties.

By suitably choosing the compounds in the composition having the general formula $AO_x\text{-}(L\text{-}Me^{n+})_i$ it is possible to obtain deodorizing products having a great cutaneous compatibility, a great efficacy in deodorizing the skin of a user thereof, and also a great efficacy in avoiding any microbial growth.

In the general formula $AO_x\text{-}(L\text{-}Me^{n+})_i$, $AO_x$ may be for example titanium dioxide ($TiO_2$), zinc oxide (ZnO), stannic oxide ($SnO_2$), zirconium dioxide ($ZrO_2$), and colloidal silica ($SiO_2$); $Me^{n+}$ may be for example a transition metal ion, for example $Ag^+Cu^{++}$.

Bifunctional molecules L may be organic or organometallic molecules, such as complexes of the transition metals.

The ligand L may be provided with different suitable functional groups, first functional group binding to the $AO_x$ oxide, and second functional group binding the $Me^{n+}$ ions.

The first functional group may be chosen in a group comprising: carboxyl (—COOH) (or carboxylate), phosphonic (—$PO_3H_2$) (or phosphonate), or boronic (—$B(OH)_2$) (or boronate), dipyridyl group, terpyridyl group.

The second functional may be chosen in a group comprising: $Cl^-$, $Br^-$, $I^-$, S, $CNS^-$, $NH_2$, N, $CN^-$ and $NCS^-$.

Said dipyridylic or terpyridylic group may be substituted by a carboxyl group, for example in a para position with respect to the pyridine nitrogen.

If more than one dipyridylic group or terpyridylic group is present, one of these groups may be unsubstituted.

The bifunctional ligands L of organic type can be selected in a group comprising:

nitrogen-containing heterocycles having 6 to 18 members, for example pyridine, dipyridyl, or terpyridyl, possibly substituted with one or more substituents, selected for example between: carboxyl (—COOH), boronic (—$B(OH)_2$), phosphonic (—$PO_3H_2$), mercaptan (—SH), and hydroxyl (—OH);

$C_6$ to $C_{18}$ aryls, for example selected from: phenyl, naphthyl, biphenyl, and possibly substituted with one or more substituents selected for example between: carboxyl (—COOH), boronic (—$B(OH)_2$), phosphonic (—$PO_3H_2$), mercaptan (—SH), and hydroxyl (—OH);

$C_2$ to $C_{18}$ monocarboxylic and dicarboxylic acids, possibly substituted with one or more mercaptan groups (—SH) and/or hydroxyl groups (—OH).

pyridine, dipyridyl, or terpyridyl, functionalized with carboxyl groups, boronic groups, or phosphonic groups;

mercaptosuccinic acid, 11-mercaptoundecanoic acid, mercaptophenol, 6-mercaptonicotinic acid, 5-carboxypentanethiol, mercaptobutyric acid, and 4-mercaptophenylboronic acid.

The first functional group and the second functional group of ligand L may also be both coordinated at a metallic centre (M) of the ligand L.

The metallic element of the ligand L may have a coordination of the octahedral type or different kind of coordination corresponding to tetrahedral geometry, rectangular planar, square planar geometry, bipyramidal trigonal geometry, or pyramidal geometry with a square or rectangular base, and any of the metals which are in the first, second, or third row of transition metals in the periodic table of the elements and which can give rise to stable bifunctional molecules of the type described may be used.

The transition metal coordinated by the ligand L can be selected from: Cr, Mn, Fe, Co, Ni, Cu, Zn, Ru, Rh, Pd, Re, Os, Ir, and Pt.

The ligand L may have a negative charge, and may form salts with cations, for example organic cations such as tetraalkylammonium cations.

By suitably choosing the atom of the metal ion $Me^{n+}$ and the metal or metalloid oxide $AO_x$ a composition can be obtained having antibacterial, antiviral, antimycotic, microcide, photocatalytic, anti-pollution properties.

In one embodiment, ion $Me^{n+}$ is chosen between $Ag^+$ and/or $Cu^{++}$ having antibacterial, antimycotic, antiviral, activity.

In another embodiment metal oxide $AO_x$ comprises $TiO_2$, for example with titanium in Anatase form, therefore an anti-pollution, photocatalytic composition can be obtained.

Such composition has particle size less than 30 nm, in particular less than 15 nm.

In a version quaternary ammonium salts may be added to the composition having the general formula $AO_x\text{-}(L\text{-}Me^{n+})_i$ so enhancing the antiviral, antibacterial, antimicrobial, antimycotic properties of the composition.

Quaternary ammonium salts, are positively charged polyatomic ions of the structure $NR_4^+X^-$ with R1, R2, R3, R4 being alkyl groups, and $X^-$ a suitable anion, for example chloride anion $Cl^-$. Any or all of the R groups may be the same or different alkyl groups.

Many of quaternary ammonium salts are widely used, for example chloride ammonium salts.

Quaternary ammonium salts are used for example as disinfectants, surfactants, fabric softeners, antistatic agents (e.g. in shampoo).

Adding suitable quaternary ammonium salts to the composition having the general formula $AO_x\text{-}(L\text{-}Me^{n+})_i$ it is possible to improve the stability of suspensions, or emulsions or solutions of the composition having the general formula $AO_x$-$(L-Me^{n+})_i$, and also to enhance the property thereof, increasing the antiviral, antibacterial, antimicrobial, fungicidal properties.

Moreover, by suitably choosing quaternary ammonium salts, it is also possible to enhance the cleaning properties of a detergent product.

For example tetraalkylammonium salt, and/or alkylammonium salts, and/or benzalkonium chloride, may be added to the composition having the general formula $AO_x$-$(L-Me^{n+})_i$.

With such a composition both transparent suspensions and milky suspensions can be obtained, such a composition may be dissolved both in aqueous solvents and in polar solvents, and both in organic solvents and inorganic solvents.

With such a composition, emulsions, such as creamy emulsions may be obtained.

Studies have demonstrated that a formulation comprising a product having the general formula $AO_x$-$(L-Me^{n+})_i$ is efficacious against several different microorganisms such as for example bacteria, fungi, sponge, mildews, and also for removing organic and inorganic pollutions.

For example efficaciousness against HSV-1 (Herpes Simplex Virus-1), Adenovirus, Poliovirus, Aviaria virus, *Legionella pneumophila, Pseudomonas aeruginosa, Staphilococcus aureus, Enterococcus faecalis, Escherica Coli, Salmonella enteridis* D1, *Listeria monocytogenes, Candida albicans, Aspergillus niger* has been demonstrated.

Therefore a coating product, painting product, a material, a cleansing product, a sterilising product, topical-treatment product, deodorizing product, objects, items effective in removing such microorganisms and in avoiding further proliferation thereof can be obtained.

The invention may be better understood and implemented with reference to the following examples and attached Figures in which.

Figure 1:
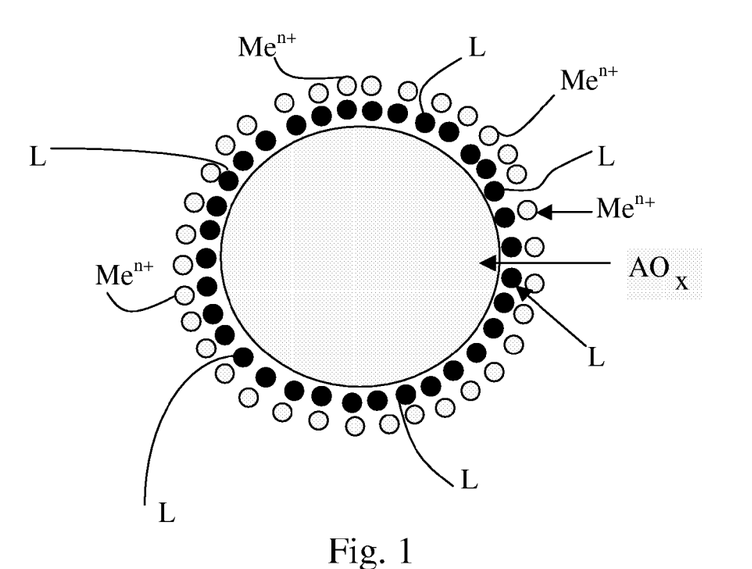
FIG. 1 schematically illustrates the structure of a composition having the general formula $AO_x$-$(L-Me^{n+})_i$.

With reference to FIG. 1 there is schematically shown the structure of a composition having the general or molecular formula $AO_x$-$(L-Me^{n+})_i$.

$AO_x$ is a metal or metalloid oxide in which x indicates the number of the Oxygen atom(s) (O) bonded to the metal (A) atom, $AO_x$ may be, for example, titanium dioxide ($TiO_2$), zinc oxide (ZnO), stannic oxide ($SnO_2$), zirconium dioxide ($ZrO_2$), and colloidal silica ($SiO_2$). $Me^{n+}$ is a metal ion, having antibacterial, antiviral, antimycotic activity, for example $Ag^+$, $Cu^{++}$.

L is a bifunctional molecule that could bind both metal oxide or metalloid oxide ($AO_x$) and the metal ion ($Me^{n+}$), and i is the number of ($L-Me^{n+}$) groups bound to the metal oxide $AO_x$; the value of the parameter i depends on various factors, such as the size of the nanoparticle of $AO_x$, the nature of the, molecule L.

Figure 2:
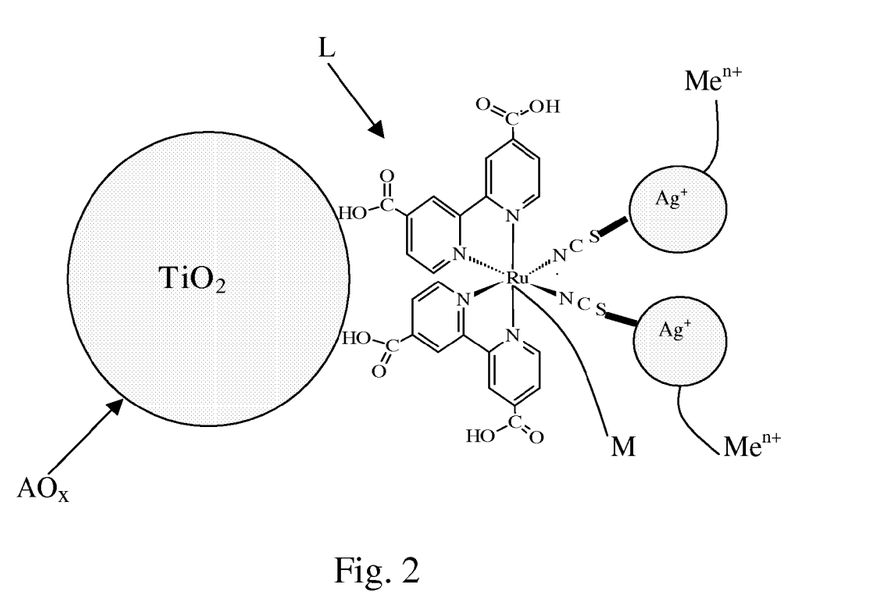
FIG. 2 a schematic representation of a particular composition having the general formula $AO_x$-$(L-Me^{n+})_i$.

Bifunctional molecules L may be organic or organometallic molecule, as in the example in FIG. 2, such as complexes of the transition metals.

Ligand L may be provided with different suitable functional groups, first functional group such as carboxyl (—COOH) (or carboxylate), phosphonic (—$PO_3H_2$) (or phosphonate), or boronic (—$B(OH)_2$) (or boronate), dipyridyl group, terpyridyl group, bonding to the $AO_x$ oxide, and second functional group such as $Cl^-$, $Br^-$, $I^-$, $CNS^-$, $NH_2$, $CN^-$ and $NCS^-$, bonding the $Me^{n+}$ ions.

In one embodiment, said dipyridylic or terpyridylic group is substituted with carboxyl group, for example in para position with respect to the pyridine nitrogen.

In the case in which more than one dipyridylic group ar terpyridylic group is present, one of these groups may be unsubstituted.

First functional group and second functional group of ligand L may also be both coordinated at a metallic center (M) of the ligand L, as in the case in FIG. 2.

The transition metal coordinated by the ligand L can be selected from: Cr, Mn, Fe, Co, Ni, Cu, Zn, Ru, Rh, Pd, Re, Os, Ir, and Pt.

The ligand L may have a negative charge, and may form salts with cations, for example organic cations, in particular quaternary ammonium cations, such as tetraalkylammonium cations.

Such composition may be mixed with cationic surfactants, such as alkylammonium salts, benzalkonium chloride, that would also enhance the bactericidal activity of the composition In FIG. 2, there is shown an example of composition having the general formula $AO_x$-$(L-Me^{n+})_i$ in which metal oxide $AO_x$ is $TiO_2$, ion $Me^+$, is $Ag^+$ and ligand L is a metallorganic molecule having the general formula $Ru(H_2dcb)_2(NCS)_2$, in which $(H_2dcb)_2$, 2,2-dipyridyl-4,4-dicarboxylic acid is the first functional group of the ligand L and $(NCS)_2$ is the second functional group, and the first and second functional groups are coordinated by a metal atom M of ruthenium (Ru).

As can be seen from FIG. 1, several molecules of ligand L, together with several metal ions $Me^+$, are bound to metal oxide $AO_x$ and are arranged so that almost all the surface of the and metal oxide $AO_x$ is covered by ligand L and, therefore by ions $Me^+$.

This is due to the small dimensions if the ligand L and of the metal ion $Me^+$, which may be of the order of picometers, therefore each molecule of metal oxide $AO_x$ can be homogeneously covered by metal ion $Me^+$.

Furthermore, owing to the very small dimensions of the molecules contained composition $AO_x$-$(L-Me^{n+})_i$ nanoparticles are obtained that can be added to a material and intimately mixed to it, obtaining a material, for example a plastic with homogeneous properties.

For the same reason very homogeneous emulsions, or suspensions, or solutions in many different solvents may be obtained with the composition $AO_x$-$(L-Me^{n+})_i$.

Such composition can be spread, or applied to a surface allowing a very homogeneous coverage and/or coating of the surface to be obtained.

Compositions having the general formula $AO_x$-$(L-Me^{n+})_i$ have particle size less than 40 nm, for example less than 30 nm, in particular less than 15 nm.

Therefore very thin and homogenous films homogeneously covering a surface can be obtained.

Composition having the general formula $AO_x$-$(L-Me^{n\pm})_i$ may be used for obtaining suspensions both transparent and milky, both in aqueous and polar solvents, both in inorganic and organic solvents, such suspension being stable over time.

For obtaining suspension of the composition having the general formula $AO_x$-$(L-Me^{n+})_i$ a metal or metalloid oxide $AO_x$ is mixed with a Ligand L, and with a solution into which ion $Me^+$ are dissolved.

Oxides $AO_x$ are usually available as suspension, for example colloidal suspensions, or also in powder form.

Colloidal suspension based, for example, on colloidal silica, and/or stannic dioxide are commercially available.

Suspension based on titanium dioxide and/or zirconium dioxide may be also prepared, for example as explained thereafter.

The afore mentioned suspension may be transparent or opaque, or milky and would affect the colour properties of the final suspension prepared.

The suspension of the metal or metalloid oxide $AO_x$ are properly mixed with a suitable Ligand L so that a certain number of molecules of the ligand may be absorbed on the surface of a molecule of oxide $AO_x$, as can be seen from the FIG. 1, and explained in the following examples.

The number of molecules L absorbed to a molecule of the oxide $AO_x$ depends on the particular oxide $AO_x$ used.

Thereafter an alcoholic solution containing the ions $Me^{n+}$ of a suitable metal is mixed, so that the metal ions may be absorbed on the molecule L, as can be seen in the FIG. 1.

The absorption of the ligand L on the molecule of the oxide $AO_x$ requires about 12-36 hours, whereas the absorption of the metal ions $Me^{n+}$ is substantially an instantaneous reaction.

Thereafter stable suspensions are obtained in which the ligand L is bound both to the oxide $AO_x$ and to the metal ions $Me^{n+}$, such suspensions may be used for obtaining many different products, for example the products cited above and in the uses above specified.

In some other cases oxide $AO_x$ in powder form may be added to a solution containing the ligand L and therefore an alcoholic solution of metal ions $Me^{n+}$ may be added.

In some other cases cationic surfactants may be absorbed on to oxide $AO_x$ and therefore a ligand L, for example in suspension and/or in solution, and an metal ions $Me^{n+}$, for example in alcoholic solution, may be added and mixed so that the absorption reactions may take place.

The presence of cationic surfactants may enhance the absorption of the ligand L to the oxide $AO_x$ and also the absorption of the metal ions $Me^{n+}$ on the ligand L.

Cationic surfactants may also improve the solubility of the components into the suspensions, improving the stability thereof, and also enhance the antibacterial, antimycotic, antimicrobial properties of the suspensions obtained.

After the composition having the general formula $AO_x$-(L-$Me^{n+}$)$_i$ has been obtained in any desired form, for example a suspension of a composition having the general formula $AO_x$-(L-$Me^{n+}$)$_i$, such composition may be used for obtaining for example paints.

Such composition may be added to any desired known paint thus obtaining a paint having anti-bacterial, antimicrobial, antimycotic, self-cleaning, anti-polluting properties.

Otherwise, such composition may be added during a desired stage of a process for producing paint.

In case the particular solvents used in the preparation of the suspension of the composition, and or the form of the composition may be chosen in view of a compatibility with the ingredients of the particular paint that it is desired to obtain.

The same applies when a cleansing product is produced using the composition having the general formula $AO_x$-(L-$Me^{n+}$)$_i$.

In fact, the composition having the general formula $AO_x$-(L-$Me^{n+}$)$_i$ may be added to a known cleansing product so obtaining a cleansing product having anti-bacterial, antimicrobial, antimycotic, self-cleaning, anti-polluting properties.

Otherwise the composition having the general formula $AO_x$-(L-$Me^{n+}$)$_i$ may be added to any desired stage of the process for producing a cleansing product to the ingredients of the cleansing product. Moreover by suitably choosing the form of the composition having the general formula $AO_x$-(L-$Me^{n+}$)$_i$ and/or the particular solvent(s) used for preparing a suspension thereof, a wide range of cleansing products may be obtained.

Moreover, after the composition having the general formula $AO_x$-(L-$Me^{n+}$)$_i$ has been obtained in any desired form, such as suspension, emulsion, solution, such composition may be added to the ingredients for preparing topical-treatment products, for example, a cream, a night cream, a lenitive cream or gel, a moisturizing cream or gel, obtaining a topical-treatment product having curative properties.

Such a composition may also be added to the ingredients for preparing curative topical-treatment products, for example to a burn cream, enhancing the curative properties thereof and conferring to the curative topical-treatment product antimicrobial, antibacterial, antimycotic, antiviral properties.

EXAMPLE 1

Transparent Suspensions Based on $TiO_2$

Into a beaker there were charged 300 mL distilled $H_2O$ and 2.1 mL of a strong acid, e.g. concentrated $HNO_3$ (65% w/w). Over a period of 10 min, 50 mL titanium isopropoxide (supplied by Fluka) was added under stirring, by means of a dropping funnel.

A white milky precipitate of $TiO_2$ was formed.

The mixture was then heated at 80° C. for 8 to 12 hours, taking care to maintain the stirring and the temperature constant.

During the heating, the precipitate redissolves, and the mixture took on an opalescent appearance.

During the phase of heating, the colloidal suspension was concentrated to a final volume of 100 to 200 mL, corresponding to a $TiO_2$ concentration of 150-75 g/L.

The nanoparticles of titanium dioxide obtained at the end of the process had a diameter in the range 6 to 15 nm.

The suspension concentrated to 100 mL was then diluted by addition of distilled water and ethanol, to give a final transparent solution (pH≈2) that has a concentration of $TiO_2$ of 1.5% and a percentage of alcohol comprised between about 10% to about 50%, for example of about 25%.

EXAMPLE 2

Transparent Suspensions Based on $ZrO_2$

Into a beaker there were charged 300 mL distilled $H_2O$ and 2.1 mL of a strong acid, e.g. concentrated $HNO_3$ (65%).

Over a period of ca. 10 min, 76 mL zirconium tetraisopropoxide (70% in isopropanol) was added under stirring, by means of a dropping funnel.

A white milky precipitation of $ZrO_2$ was seen to form almost immediately.

The mixture was then heated at 90° C. for 8 to 12 hours, taking care to maintain the stirring and to maintain constant temperature.

During the heating, the precipitate redissolves, giving rise to a milky-appearing suspension, which was concentrated to 140-280 mL, corresponding to a $ZrO_2$ concentration of 150-75 g/L.

The suspension concentrated to 140 mL was diluted with distilled water and ethanol to obtain 1.4 L of an opalescent suspension (pH≈2) having a concentration of $ZrO_2$ of 1.5% and a percentage of alcohol comprised between about 10% and about 50%, for example of about 25%.

EXAMPLE 3

Opaque Suspensions Based on $TiO_2$

Neutral aqueous opaque suspensions based on titanium dioxide can be obtained by adding titanium dioxide P25 to aqueous solutions of "Triton X 100" (supplied by Fluka).

Neutral aqueous opalescent suspensions based on titanium dioxide may also be prepared from peroxytitanic acid by a modification of a procedure reported in the literature (Ichinose, H., Terasaki, M., and Katsuki, H., 1996 J. Ceramic Soc. Japan, 104, 715).

In a typical preparation, 150 mL $TiCl_4$ in 20% HCl is charged to a 1 L beaker, and 826 mL $NH_4OH$ diluted 1:9 with distilled water is added to this solution.

The pH of the resulting solution is neutral (pH=7), and titanic acid, $Ti(OH)_4$, is precipitated.

This precipitate is white and has the consistency of a gel. The precipitate is collected on a filter of porosity G3, and is washed with 750-1000 mL distilled water (until complete elimination of the chloride is achieved, as can be demonstrated by treating the liquid filtrate with $AgNO_3$).

The precipitate comprised of titanic acid, $Ti(OH)_4$, is collected and is suspended in 200 mL distilled water having conductivity less than 1.5 mS and having pH comprised in the interval 5-7; to this there is slowly added over a period of 20-30 minutes 92 mL of 30% $H_2O_2$.

The dissolution of the precipitate is noted, and the formation of a yellow-coloured solution containing peroxytitanic acid, of general formula $[Ti_2(O)_5(OH)_x]^{(x-2)-}$, where x is in the range 3-6.

Finally the solution is heated 1 hr at 70° C. to decompose the excess $H_2O_2$, and is then autoclaved 8 hr at 120° C.

In this phase of the procedure, the peroxytitanic acid decomposes to titanium dioxide, principally in the allotropic form of anatase.

The resulting suspension of nanoparticles has a pH close to neutral, and an opaque appearance, and is stable over time.

Suspensions obtained according to any one of the examples 1 to 3 or suspensions obtained in any other suitable methods and containing at least metal or metalloid oxide having formula $AO_x$, or in any case metal or metalloid oxide having formula $AO_x$ in any other suitable form, for example in powder form, are made to react with a suitable bifunctional ligand (L) so that the ligand L is adsorbed on to the particles of the oxide $AO_x$.

The number of molecules of ligand L absorbed on each molecule of oxide $AO_x$ depends on the features of the ligand L and of the oxide $AO_x$.

Thereafter an aqueous or alcoholic solution containing metal ions $Me^{n+}$, for example $Ag^+$ or $Cu^{2+}$ ions, is added so that the metal ions $Me^{n+}$ are absorbed on the molecule of the Ligand L, obtaining the structure shown in FIG. 1.

Therefore a suspension, or a solution, containing a composition having the general formula $AO_x$-(L-$Me^{n+}$)$_i$ is obtained.

A cationic surfactant may then be added to the suspension of nanomaterials functionalized with metal ions $Me^{n+}$, or may be independently added to or adsorbed onto the oxide $AO_x$

EXAMPLE 4

Adsorption of 4-mercatophenylboronic acid and Ag+ ions onto "$TiO_2$ P25" (Supplied by Degussa)

To a solution containing $2*10^{-5}$ moles of 4-mercaptophenylboronic acid dissolved in 50 mL ethanol there was added 1 g of $TiO_2$ P25 (supplied by Degussa).

The suspension was stirred 24 hr. 4-mercaptophenylboronic acid has an absorption band at 255 nm, attributable to the π-π* transition in the phenolic ring.

This electronic absorption band permits the adsorption of the boronic acid onto the surface of the nanomaterial as a function of time to be monitored.

It is known that the adsorption occurs by interaction of the boronic function with the surface of the semiconductor.

The electronic absorption spectra demonstrate that the quantity of 4-mercaptophenylboronic acid adsorbed on the surface of the "$TiO_2$ P25" reaches 35% of the initial concentration in 24 hr.

The solution was centrifuged 10 min at 4000 rpm, obtaining a clear solution, the solid was washed with 20 mL ethanol, and was then re-suspended with 50 mL ethanol under stirring.

To this suspension was added $7.2*10^{-6}$ moles of a soluble silver salt, for example silver lactate or silver acetate.

The suspension obtained was white in colour, odourless, and stable over time.

A suspension containing a composition having the general formula $AO_x$-(L-$Me^{n+}$)$_i$ is obtained, in which $AO_x$ is $TiO_2$, L is 4-mercaptophenylboronic, and $Me^{n+}$ is $Ag^+$.

EXAMPLE 5

Adsorption of 4-mercaptophenylboronic acid and $Ag^+$ ions onto Transparent Suspensions of $TiO_2$ Obtained According to Example 1, and onto Products of the Ffirm NMTech 100 mL of a transparent solution of titanium dioxide prepared according to method (A) and containing 15% $TiO_2$ was diluted with 100 mL distilled water and with 200 mL of a solution of 0.052 g 4-mercaptophenylboronic acid dissolved in ethanol.

The suspension was stirred 24 hr, at the end of which period a spectrophotometric determination revealed that the boronic acid was completely adsorbed on the semiconductor nanoparticles.

The small dimensions of the nanoparticles with respect to "$TiO_2$ P25" and the consequent larger surface area of the suspended matter are responsible for the complete adsorption of the bifunctional ligand.

To the transparent odorless suspension there was added under stirring a stoichiometric amount (with respect to L) of a silver salt, e.g., silver lactate (0.06 g) or silver acetate (0.05 g).

After 1 hr of continuous stirring, there was added 10-20 mL, for example 12 mL, of a 50% (w/v) aqueous solution of benzalkonium chloride, and the suspension was stirred for an additional 1 hr.

The concentrated suspension was then diluted with distilled water and ethanol to obtain 1 L of an opalescent suspension (pH≈2) containing $TiO_2$ in a concentration of 1.5% and ethanol comprised between about 10% and about 50%, for example of about 25%.

The transparent suspension was found to be indefinitely stable.

A suspension containing a composition having the general formula $AO_x$-(L-$Me^{n+}$)$_i$ is obtained, in which $AO_x$ is $TiO_2$, L is 4-mercaptophenylboronic, and $Me^{n+}$ is $Ag^+$, and further comprising a quaternary ammonium salt such as benzalkonium chloride.

Hereinbelow, this product will be designated as "Bactercline", for the sake of brevity.

The same procedure may be employed to modify transparent suspensions of nanomaterials marketed by NM Tech Ltd.

and designated "PSO 419", wherewith the amounts of bifunctional ligand and of silver ions are adjusted based on the amount of titanium dioxide in the product.

For example, the product "PSO-419 D2" which is similar to the product prepared according to the example 1, and which has a content of $TiO_2$ of 2% and pH ca. 2, can be converted into an antibacterial and antiviral product using a method analogous to that described above.

In particular, 50 mL of "PSO-419 D2" solution containing 2% $TiO_2$ is diluted with 2.2 mg 4-mercaptophenylboronic acid ($2.05 \times 10^{-5}$ M), and the suspension is stirred 24 hr.

To the resulting odourless solution there is added $2.05 \times 10^{-5}$ M silver lactate or silver acetate.

Finally, after 1 hr of continuous stirring, 8-20 mL, for example 12 mL of an aqueous solution of dimethyl benzyl dodecyl ammonium chloride (50% w/v) is added, and the suspension is stirred for an additional period of 1 hr.

The resulting transparent suspension is indefinitely stable.

It should be noted that other opaque products marketed by NM Tech Ltd., such as "AT-01" and "AT-03", based on $TiO_2$, can be treated according to the described methods according to the present invention, to give rise to stabile suspensions or powders which have antibacterial and antiviral activity.

For example: 50 mL of a solution of "AT-01" containing 1.7% $TiO_2$ was diluted with 50 mL ethanol containing 3.8 mg of dissolved 4-mercaptophenylboronic acid ($1.9 \times 10^{-5}$ M), and the suspension was stirred 24 hr, yielding an odourless product. Then $1.9 \times 10^{-5}$ M silver lactate or silver acetate was added. The resulting suspension gave rise to a fine precipitate, after a period of time.

EXAMPLE 6

Adsorption of Cationic Surfactants onto Titanium Dioxide

Cationic surfactants with antibacterial activity are generally absorbable onto nanomaterials based on $TiO_2$, $ZrO_2$, $SnO_2$, ZnO and $SiO_2$.

The adsorption occurs nearly instantaneously onto negatively charged or neutral nanoparticles.

In the case of suspensions of nanomaterials with basic pH, the addition of benzalkonium-type salts, such as, for example, benzyl dodecyl dimethyl ammonium chloride, or benzyl hexadecyl dimethyl ammonium chloride, or benzalkonium chloride, causes precipitation of the suspension; whereas in the case of suspensions of nanomaterials with neutral or acid pH the suspension is stable.

Indirect tests of the adsorption of benzalkonium chloride on nanomaterials based on $TiO_2$ at neutral pH employ conductimetric measurements.

The association via adsorption of the benzyl dialkyl ammonium cation on the $TiO_2$ should predictably cause a reduction in conductivity, as was verified in the following experiment. A 50% (w/v) solution of benzalkonium chloride diluted 1:10 has a conductivity of 4.7 mS.

If the volume of this solution is increased by 10 to 15 mL by addition of distilled water, the conductivity is reduced to 3.90 mS. If instead the solution is diluted by adding 5 mL of a neutral suspension of titanium dioxide prepared, according for example to the example 3, from peroxytitanic acid, or the equivalent "AT-03" product at neutral pH, the conductivity measured is 3.60 mS.

The reduction in conductivity by 300 μS is attributable to the adsorption of the cationic surfactant onto the surface of the titanium dioxide.

Therefore, very stable suspension may be obtained in which the quaternary ammonium salts are absorbed in the molecule of the $AO_x$, in this case of the $TiO_2$.

Moreover, a single quaternary ammonium salt may be added or also a mixture of different quaternary ammonium salts, for example a mixture of salts with the same anion, such as chloride ammonium salts.

EXAMPLE 7

Adsorption of 2,2'-dipyridyl-4-carboxy-4'-carboxylate acid, $Ag^+$, and $Cu^{2+}$, onto "$TiO_2$ P25" (Supplied by Degussa)

The 2-2'-dipyridyl-4-carboxy-4'-carboxylate anion acid (abbreviated "Hdcb") is produced by adding one equivalent of tetrabutylammonium hydroxide (abbreviated TBAOH) to 2,2'-dipyridyl-4,4' dicarboxylic acid (abbreviated $H_2dcb$), which is scarcely soluble and is in solid form.

The ligand in the monocarboxylate form (also called "monoprotonated form"), and as a tetrabutylammonium salt (abbreviated "TBA(Hdcb)"), can thus be solubilized in methanol or ethanol and can be adsorbed on titanium dioxide.

To a solution of $1 \times 10^{-4}$ moles TBA(Hdcb) in 100 mL ethanol there was added 5 g "$TiO_2$ P25" (supplied by Degussa). The suspension was stirred 24 hr.

The ligand TBA(Hdcb) has an absorption band at 294 nm, due to $\pi$-$\pi^*$ transitions, which allows monitoring of its adsorption onto nanomaterials as a function of time.

The ligand is completely adsorbed onto the surface of the nanocrystalline substrate.

It is known that the adsorption occurs by interaction of the carboxyl functions with the surface of the semiconductor.

The suspension was then centrifuged 10 min at 4000 rpm, and the solid was washed with 50 mL methanol. The nanomaterial obtained, functionalized with the ligand (abbreviated $TiO_2$/TBA(Hdcb)), was then finally vacuum-dried at ambient temperature.

Two portions of 2 g each, of the $TiO_2$/TBA(Hdcb), were re-suspended in 100 mL ethanol.

To one suspension there was added 8 mg silver lactate, under stirring; and to the other suspension there was added 7 mg $CuCl_2$.

The two suspensions had different stabilities: the suspension functionalized with copper ions, $TiO_2$/TBA[Hdcb]/$Cu^{2+}$, remained stable, while that functionalized with silver ions, $TiO_2$/TBA[Hdcb]/$Ag^+$, precipitated over time.

EXAMPLE 8

Adsorption of Organometallic Ligands (L) and $Ag^+$ ions on Neutral Suspensions of $TiO_2$ Bifunctional organometallic ligands L, as previously disclosed can be anchored to neutral suspensions of titanium dioxide prepared, for example according to method of example 3, with the nanomaterials being suspended in alcohol solutions of a concentration of approximately $10^{-3}$-$10^{-4}$ M of the bifunctional organometallic ligands.

The suspension is stirred 12 hr, during which time the organometallic ligand L is completely adsorbed onto the surface of the nanomaterials.

The addition of stoichiometric amounts of silver with respect to the ligand L, in alcoholic solution, corresponds to formation of adducts in which the silver ion $Ag^+$ is anchored to the inorganic ligand, as illustrated schematically in FIG. 1 in the case of the complex $(H_2dcb)_2Ru(NCS)_2$ ($H_2dcb$=2,2'-dipyridyl-4,4'-dicarboxylic acid).

The presence of the carboxyl functions enables adsorption of the complex, and homogeneous covering of the nanocrystalline material, for a time of the order of 2-3 hr at 50° C., and 12 hr at ambient temperature.

In a subsequent step, a silver salt, e.g. silver nitrate, silver lactate, or silver acetate, is added to the methanolic solution, in a stoichiometric ratio of 2:1 with respect to the moles of $(H_2dcb)_2Ru(NCS)_2$.

The presence of the two NCS groups allows the $Ag^+$ ions to be instantaneously bonded as illustrated in FIG. 2.

Antibacterial and antiviral activity of the composition having the general formula general formula $AO_x$-$(L-Me^{n+})_i$ has been tested, in particular with reference to products obtained according to any one of the examples 1 to 8.

The testing was conducted by depositing films comprised of the different nanomaterials obtained according to the afore described examples on Petri capsules in contact with a number of colonies of *Escherica Coli* greater than $10^4$ cfu (colony forming units).

In all cases, complete mortality of the colonies was observed.

More thorough measurements were carried out according to the standards UNI-EN 1276 of April 2000 and UNI-EN 13697 of December 2001, for the product synthesized according to method of example 5 (product designated "Bactercline"), which product is transparent and thus applicable to a broader range of applications.

Tests have been conducted for evaluating the bactericidal, antimycotic, virucidal properties of a solution of the product named as "Bactercline" containing a composition having the general formula $AO_x$-$(L-Me^{n+})_i$, in which $AO_x$ is $TiO_2$, L is 4-mercaptophenylboronic, and $Me^{n+}$ is $Ag^+$, and, in case, further comprising a quaternary ammonium salt such as benzalkonium chloride.

Such product may be obtained in any suitable method, for example according to the methods in examples 4, 5, 6.

The bactericidal activity of "Bactercline" has been evaluated using the method of dilution and neutralization according to standard method UNI-EN 1276 of April 2000.

The following strains were used for the testing: *Pseudomonas aeruginosa, Staphylococcus aureus, Enterococcus faecalis, Escherichia coli, Salmonella enteridis* D1, *Listeria monocytogenes*.

All of the bacterial strains tested were provided by the Department of Experimental and Diagnostic Medicine, Microbiology Section, of the University of Ferrara.

The "Bactercline" product tested was diluted to 80%.

The substance being tested was deemed bactericidal if for each bacterial strain at 20° C. after a contact time of 5 min, a reduction of vitality of at least $10^5$ units obtained.

The results obtained are reported in the following Table 1.

The obtained results indicate that in all cases a reduction in vitality of greater than $10^5$ units was obtained.

TABLE 1

| MICROORGANISMS Concentration of the solution of | Logarithm of the antimicrobial activity | |
| --- | --- | --- |
| "Bactercline" | 50% | 80% |
| *Staphylococcus aureus* | >3.27 * $10^5$ | >4.02 * $10^5$ |
| *Pseudomonas aeruginosa* | >1.23 * $10^5$ | >4.00 * $10^5$ |
| *Escherichia coli* | >1.20 * $10^5$ | >4.00 * $10^5$ |
| *Enterococcus faecalis* | >1.55 * $10^5$ | >4.19 * $10^5$ |

TABLE 1-continued

| MICROORGANISMS Concentration of the solution of | Logarithm of the antimicrobial activity | |
| --- | --- | --- |
| "Bactercline" | 50% | 80% |
| *Salmonella enteridis* D1 | >1.21 * $10^5$ | >4.21 * $10^5$ |
| *Listeria monocytogenes* | >5.56 * $10^5$ | >4.24 * $10^5$ |

Based on the results obtained and the validity criteria of the tests, the "Bactercline" substance tested is bactericidal when used at a concentration of 80% (which turns out to be the maximum testable concentration), after 5 min of contact in the presence of bovine albumin at a final concentration of 0.3%, according to the method of the standard UNI-EN 1276 of April 2000.

"Bactercline" is bactericidal also when used at a concentration of 50%, after 5 min of contact in the presence of bovine albumin at a final concentration of 0.3%, according to the method of the standard UNI-EN 1276 of April 2000, since also at such a concentration a vitality reduction more than $10^5$ units is obtained.

The bactericidal activity of "Bactercline" is therefore very high.

A surface test has also been made for evaluating the bactericidal activity of "Bactercline" according to the standard method UNI-EN 13697 of December 2001.

The following strains were used in the tests: *Pseudomonas aeruginosa, Staphylococcus aureus, Enterococcus faecalis, Escherichia coli, Salmonella enteridis* D1, *Listeria monocytogenes, Legionella Pneumophila*.

The substance being tested was deemed bactericidal against the bacterial strains provided according to the European Standard if for each bacterial strain, at 20° C. after a contact time of 5 min, a reduction of vitality of at least $10^4$ units is obtained.

The results obtained are reported in the following Table 2.

Such values indicate that in all cases the decimal logarithm of the antimicrobial activity was greater than 4, and therefore that "Bactercline" is a bactericidal product. Based on the results obtained and the validity criteria of the tests, the "Bactercline" substance tested under the stated test conditions is bactericidal against the tested microorganisms, when used at a concentration of 100%, after 5 min of contact in the presence of bovine albumin at a final concentration of 0.3%, according to the method of the standard UNI-EN 13697 of December 2001.

TABLE 2

| MICROORGANISMS | Logarithm of the antimicrobial activity |
| --- | --- |
| *Staphylococcus aureus* | >4.00 |
| *Pseudomonas aeruginosa* | >4.03 |
| *Escherichia coli* | >4.02 |
| *Enterococcus faecalis* | 4.19 |
| *Salmonella enteridis* D1 | >4.21 |
| *Legionella Pneumophila* | >4.26 |
| *Listeria monocytogenes* | >4.24 |

The antimycotic, or fungicidal, activity of "Bactercline" has been evaluated using the method of dilution and neutralization according to standard method UNI-EN 1650 of October 2000.

The following strains were used for the testing: *Candida albicans, Aspergillus niger.*

The strains tested were provided by the Department of Experimental and Diagnostic Medicine, Microbiology Section, of the University of Ferrara.

The substance being tested was deemed fungicidal if, for each of the mycotic strains, at 20° C. after a contact time of 15 min, a reduction of vitality of at least $10^4$ units is obtained. The tests have been repeated for different values of the concentration of "Bactercline", and the results obtained have been reported in table 3.

TABLE 3

| TEST MICROORGANISMS Concentration of "Bactercline" | REDUCTION IN VITALITY | | |
| --- | --- | --- | --- |
| | 25% | 50% | 80% |
| Candida albicans | >1.13 × $10^4$ | >1.13 × $10^4$ | >1.13 × $10^4$ |
| Aspergillus niger | <1.87 × $10^3$ | >1.37 × $10^4$ | >1.37 × $10^4$ |

Based on the results obtained and the validity criteria of the tests, the "Bactercline" substance tested is antimycotic against *Candida albicans* at concentrations of 25%, 50%, and 80%, and against *Aspergillus niger* at concentrations of 50% and 80% (which turns out to be the maximum concentration testable), after 15 min of contact in the presence of bovine albumin at a final concentration of 0.3%, according to the method of the standard UNI-EN 1650 of October 2000.

The antimycotic activity of "Bactercline" has been evaluated also using the surface test according to standard method UNI-EN 13697 of December 2001.

The following strains were used for the testing: *Candida albicans, Aspergillus niger.*

The strains tested were provided by the Department of Experimental and Diagnostic Medicine, Microbiology Section, of the University of Ferrara.

The substance being tested was deemed antimycotic if the logarithm of the antimicrobial activity against the microbial strains provided according to the European Standard was greater than or equal to 3, for 15 minutes of contact at 20° C. The results of the tests have been reported in Table 4.

TABLE 4

| | Logarithm of the antimicrobial activity | |
| --- | --- | --- |
| TEST MICROORGANISMS | | |
| Concentration of "Bactercline" | 50% | 100% |
| Candida albicans | 2.02 | >3.18 |
| Aspergillus niger | 1.14 | >3.04 |

Based on the results obtained and the validity criteria of the tests, the "Bactercline" substance tested under the stated test conditions is antimycotic against *Candida albicans* and *Aspergillus niger*, when used at a concentration of 100%, after 15 min of contact in the presence of bovine albumin at a final concentration of 0.3%, according to the method of the standard UNI-EN 13697 of December 2001.

Moreover the virucidal activity of "Bactercline" has been tested.

The experiments described hereinbelow demonstrate that the product "Bactercline", in very low concentrations, has high virucidal activity against the HSV-1 virus (herpes simplex virus-1).

Various amounts of viral suspensions were prepared in modified Dulbecco medium (D-MEM) to which 1% of bovine fetal serum (BFS) had been added.

A virus concentration (virus titre) of $1 \times 10^6$ cytolytic plaque forming units (Pfu) was used. Different amounts of "Bactercline" were added to different samples, with pre-treatment times of 1 and 5 hr.

Untreated viral suspensions were maintained as a control. After a period of incubation at ambient temperature, all of the samples were diluted to known volumes, for determining the titres of the virus.

The viral titres of the controls and of the samples treated with "Bactercline" e were determined by the method described hereinbelow.

In determining the viral titre, the number of infectious present in 1 mL of solution may be calculated.

A method used provided for determining the number of cytolysis plaques produced by a sufficiently diluted viral suspension and placed in contact with a monolayer of cells. In this series of experiments, renal cells of African Monkey were used (Vero).

The cells were cultured at 37° C., in the presence of 5% of $CO_2$ in "D-MEM" to which 10% BFS, 1% L-glutamine, and 1% penicillin/streptomycin had been added.

The determination of the titre was carried out on plates having 12 wells.

When the cultures were nearly confluent, the viral stock was diluted to known concentrations in a medium containing 2% BFS.

For each dilution, 2 wells on the plate were inoculated. After incubation 1 hr at 37° C., the inoculum was drawn off and the infection was blocked by adding a medium containing 1% BFS and 2% human gamma globulin, having the function of inhibiting formation of secondary plaques.

The inoculated cultures were incubated at 37° C. for 2 days, and were monitored until the lysis plaques were visible. At this point, the cells were fixed and were stained with gentian violet.

Under an optical microscope, the plaques present in the wells were counted and this count was multiplied by the dilution factor, to obtain the viral titre, in units of Pfu/mL.

The "Bactercline" product in the amount of 10 and 50 microliters was contacted with HSV-1 having a viral titre of $1 \times 10^6$ Pfu.

The incubation was carried out in 1 mL of D-MEM medium to which 1% of BFS had been added.

Two different incubation times were used: 1 hr and 5 hr. After the given incubation period, the virus was diluted to concentrations of $1 \times 10^3$ and $1 \times 10^2$ Pfu, and the nearly confluent cultures were inoculated.

As shown in Table 5, the cells inoculated with the virus pretreated with "Bactercline" did not have lysis plaques, for either of the pretreatment times and either of the virus dilutions.

The tests on the antiviral activity of the "Bactercline" product shows that the product has antiviral activity for direct contact with HSV-1 virus even at extreme dilutions of the product, at a contact time of 1 hr.

The experiments carried out, the results of which have been represented in following table 5, demonstrated that at a level of dilution of the product of on the order of 1:100 one achieves nearly total mortality of the viral particles.

TABLE 5

Pretreatment of HSV-1 in a titre of 1 × 10⁶ with 10 μL and 50 μL di the product being tested:
Dilution of the HSV-1 (1 × 10³ Pfu)

| Mean of the controls (Pfu) | | Mean of the samples treated with 10 μL (Pfu) | | Inhibition of plaque formation (%) | Mean of the samples treated with 50 μL (Pfu) | | Inhibition of plaque formation (%) | Viral titre of the controls | |
|---|---|---|---|---|---|---|---|---|---|
| 1 hr | 5 hr | 1 hr | 5 hr | 1 hr, 5 hr | 1 hr | 5 hr | 1 hr, 5 hr | 1 hr | 5 hr |
| 63 | 78 | | | 100 | 0 | | 100 | 2.63 × 10⁵ | 1.78 × 10⁵ |

EXAMPLE 9

Method for Producing a Cream for Topical Use Containing the Composition Having the General Formula $AO_x\text{-}(L\text{-}Me^{n+})_i$ Using the composition having the general formula $AO_x\text{-}(L\text{-}Me^{n+})_i$ many different kind of topical-treatment products for topical use may be obtained, since the composition having the general formula $AO_x\text{-}(L\text{-}Me^{n+})_i$ may be suitably mixed with many different substances. For example a topical-treatment cream to be used for treating acne may be obtained.

In the following table 6 the percentage content of a cream for topical use for treating acne is indicated.

TABLE 6

| Compound | Percentage [%] | Physical State | Adding phase |
|---|---|---|---|
| Water | 72.23 | liquid | B |
| PPG-15-sterarylether | 15 | liquid | A |
| Steareth-2 | 5 | waxy solid | A |
| $AO_x\text{-}(L\text{-}Me^{n+})_i$ | 2 | powder | C |
| Cetearyl alcohol | 1.6 | waxy solid | A |
| Benzalkonium chloride | 1.2 | Liquid | C |
| Steareth-21 | 1 | waxy solid | A |
| Dimethicone | 1 | liquid | A |
| Methylparaben | 0.3 | powder | B |
| Propylparaben | 0.2 | powder | B |
| Citric acid | 0.2 | crystalline solid | B |
| Sodium dehydroacetate | 0.15 | powder | B |
| Butylated Hydroxyanisole (BHA) | 0.05 | crystalline solid | A |
| Butylated Hydroxytoluene (BHT) | 0.05 | crystalline solid | A |
| 2,4 Bromonitropropandiol | 0.02 | crystalline solid | C |

The aforementioned compounds are weighed and dosed.

A turboemulsifier is heated up to a temperature of about 65°-70° C.

Phase "A": The compounds having the value "A" in the fourth column of the above table 1 are introduced into a turboemulsifier and mixed together. The turboemulsifier is heated up to a temperature of about 70°-80° C., so that the compounds in the turboemulsifier melt. Complete melting of the compounds has to be achieved, so that better mixing can be obtained.

Phase "B": A further turboemulsifier is heated up to a temperature of about 75°-80° C. The compounds having the value "B" in the fourth column of the above table 6 are introduced into the further turboemulsifier, mixed together.

As the compounds in the turboemulsifier and in the further turboemulsifier reach the desired temperature values, both the turboemulsifier and the further turboemulsifier are closed, and operated so that the respective compounds in the turboemulsifier and in the further turboemulsifier can be mixed and homogenized.

Thus, a vacuum pump, connected to the turboemulsifier is operated, and the compounds in the further turboemulsifier are poured in the turboemulsifier, i.e. compounds of phase "B" are poured in the compounds of phase "A".

The turboemulsifier is operated for a small number of minutes so that the compounds of phase "A" and of phase "B" mix and homogenize together, the real mixing of the mixture can be checked and, if necessary, the turboemulsifier may be newly operated.

After the desired mixing of the mixture is obtained, the vacuum pump is operated, and the turboemulsifier is cooled down to a temperature of about 45° C.-50° C.

After such a temperature value is reached, the vacuum pump is switched off and the compounds having the value "C" in the fourth column of the above table 6 are introduced into the turboemulsifier.

The turboemulsifier and the vacuum pump are both operated so that the compounds can be mixed and homogenized together, and the turboemulsifier is cooled during the homogenizing, down to a temperature of about 20°-30° C.

Such a temperature value is maintained for a certain time interval during which the compounds are continuously mixed.

After a given time interval has elapsed, the product may be poured out form the turboemulsifier and analyzed.

Analysis carried out have demonstrated that the product is very stable over time and can be packed in subsequent packing operations and stocked without any risk of separations of the single compounds of the product.

The product obtained, referred to hereinafter as "Bactercline acne" for the sake of brevity, is an emulsion containing the composition having the general formula $AO_x\text{-}(L\text{-}Me^{n+})_i$ and additives and/or other active principles that can be used for preparing topical-treatment products.

Such an emulsion is in creamy state and can be used for treating many diseases, and in particular, acne diseases.

Owing to the very limited dimension of the composition having the general formula $AO_x\text{-}(L\text{-}Me^{n+})_i$ and the features thereof, an emulsion having very homogenous features is obtained.

As the composition having the general formula $AO_x\text{-}(L\text{-}Me^{n+})_i$ may for example be used a composition containing titanium dioxide ($TiO_2$) as $AO_x$ silver perchlorate ($Ag^+ClO_4^-$) as $Me^{n+}$ and a bifunctional ligand L suitable to bond both the titanium dioxide and the silver perchlorate.

In one embodiment, 2 g of the composition having the general formula $AO_x\text{-}(L\text{-}Me^{n+})_i$ contain 1.998 g of $TiO_2$, 0.0084 g of $AgClO_4$, and 0.0062 g of 4-mercaptophenyl boronic acid as bifunctional ligand L.

A quaternary ammonium salt is also present, i.e. benzalkonium chloride.

Similar preparations may also be obtained using as bifunctional ligand L 6-mercaptonicotinic acid, and/or 11-mercaptoundecanoic acid, and/or mercaptosuccinic acid.

"Bactercline acne" is a creamy, odourless emulsion, having a white colour, with a density of about 0.995-1.005 g/cm$^3$, and a viscosity of about 50,000-60,000 centipoises.

The creamy emulsion obtained may be spread on the skin, for example twice a day, owing to the physical features thereof the cream may be spread very easily, and forms on the skin of a user a protective layer, that is invisible and thus not unsightly, and that disinfects the skin allowing the acne diseases to be treated.

Spreading "Bactercline acne" twice a day on the skin affected by acne and/or herpes, skin lesions due to acne and/or herpes are healed, and any further contagion of different areas of the skin of the user is prevented.

The cream forms on the skin of a user a protective layer that has a multiple action: it protects the area of the skin lesions from any external infections, and/or microbial infections, protects such area from any external aggression due, for example, to the wind and/or sun radiation, and also prevents any contagion spreading over different areas of the skin of the user, and also any microbial proliferation over such area.

This enables a very fast regeneration of the damaged skin, and the spread of the contagion to be prevented, and enables therefore the skin diseases to be successfully treated.

Such a cream may also be usefully used for treating herpes virus topical diseases.

By spreading the cream twice a day on the skin affected by herpes, skin lesions due to herpes are healed, and any further contagion in different areas of the skin of the user is prevented.

The process for producing the cream is very simple and the phase of adding the composition having the general formula $AO_x\text{-}(L\text{-}Me^{n+})_i$ does not interfere with an usual process for producing a topical-treatment product.

Therefore, similar process may be used for producing many different topical-treatment products containing the composition having the general formula $AO_x\text{-}(L\text{-}Me^{n+})_i$ and additives or active principles different from those described above.

Topical-treatment products that can be used for different topical uses and for treating many different diseases may be thus obtained.

Furthermore, the composition having the general formula $AO_x\text{-}(L\text{-}Me^{n+})_i$ may be added to many different kind of topical-treatment products, such as vanishing cream, shaving cream, anti-wrinkle cream, moisturizing cream, protective cream, daily cream, or night cream, giving to the topical-treatment product the antibacterial, antiviral, antimicotic properties.

Moreover, the composition having the general formula $AO_x\text{-}(L\text{-}Me^{n+})_i$ may also be added to topical-treatment products in other forms than cream, such as for example gel, tissues soaked with active principles, wipes, patches, liquid crystals, liquid compositions with two or more distinct layers, dispersions, emulsions, suspensions, foams, microbeadlets, microspheres, granules, microgranules, microemulsions; nano emulsions, multiple emulsions, e.g. water-in-oil-in-water, encapsulated compositions.

Moreover, the topical-treatment product produced according to the aforementioned process and containing the compounds of the aforementioned table is efficacious against the following microbes: bacteria: *Pseudomonas aeruginosa, Staphylococcus aureus, Staphylococcus epidermidis, Enterococcus faecalis, Escherichia coli, Salmonella enteriditis D*1, *Listeria monocytogenes, Legionella Pneumofila*; fungi: *Candida albicans, Aspergillus niger*; virus: Herpes virus.

Tests have been conducted to evaluate the virucidal efficacy of "Bactercline acne" against different viruses and in particular against Poliovirus and Adenovirus.

Tests were conducted according to the standard procedure described in "European Standard EN14476, May 2002 (phase 2; step 1) edited by the European Standardization Committee to evaluate the virucidal activity of "Bactercline acne".

A certain quota of a viral suspension was added to "Bactercline acne" both in "clean state", i.e. in a water solution containing 0.3 g/l of bovine albumin, and in "dirty state", i.e. in a water solution containing 3.0 g/l of bovine albumin and 0.3 ml of erythrocytes.

Suspension containing Adenovirus type 5 (ATCC VR5) and Poliovirus 1 Sabin strain having a titre, evaluated as $\text{Log}_{10}$ of $\text{ID}_{50}$, respectively of Adenovirus type 5 5-8.15 for Adenovirus type 5 and 1-8.20 for Poliovirus 1 Sabin strain, and with different dilution ratio comprised between 0 (undiluted suspension) and $10^{-4}$, were prepared, such suspensions were brought into contact with layers of HeLa cells at about 90%, those cells had been cultivated in MEM with 2% FBC, to evaluate the maximum viral concentration that does not cause morphological mutation in the cells.

Such a maximum concentration is $10^{-1}$.

Therefore in tests undiluted suspensions of viruses have been used.

The viral suspensions and "Bactercline acne" were kept in contact at a temperature of about 20° C. for preset time intervals: 1 min, 10 min, 30 min, 60 min.

After each one of said time intervals a certain quantity of the mixture containing the viral suspension and "Bactercline acne" was removed, diluted using a 1:10 dilution ratio with a Minimal Essential Medium (MEM) and 2% of Fetal Calf Serum (FCS) to block the virucidal activity, and then analyzed for evaluating the virucidal activity.

The virucidal activity was evaluated calculating the $\text{ID}_{50}$ i.e. the dilution of the viral suspension that causes cytopathic effects in 50% of the samples, as according to the "Spearman-Karber method".

The results of the tests are shown in the following table 7 and table 8 respectively for suspension of Poliovirus and Adenovirus 5.

TABLE 7

| Contact time | Viral titre "dirt" | Viral titre "clean" |
|---|---|---|
| 60 min | −1.5 | −1.1 |
| 30 min | −2.8 | −2.0 |
| 10 min | −4.0 | −3.0 |
| 1 min | −5.5 | −4.8 |

TABLE 8

| Contact time | Viral titre "dirt" | Viral titre "clean" |
|---|---|---|
| 60 min | −1.0 | −1.0 |
| 30 min | −2.0 | −1.5 |
| 10 min | −4.1 | −2.5 |
| 1 min | −4.8 | −4.5 |

The values in second and third column of the aforementioned tables 7, 8, indicate the negative logarithm of the 50% of the end-point.

The results obtained, show that a reduction higher than 4 $Log_{10}$ of the viral titre of the suspensions contacted with "Bactercline acne" has been obtained for both the viral suspensions either in "clean" and in "dirty" state samples; the samples had contact time interval of about 10 min.

Therefore a high virucidal activity of "Bactercline acne" has been demonstrated.

The methodology of such tests has been verified for validating the results obtained. Such a validation has obtained positive results.

EXAMPLE 10

Method for Producing a Topical-Treatment Product Containing the Composition Having the General Formula $AO_x\text{-}(L\text{-}Me^{n+})_i$ Using the composition having the general formula $AO_x\text{-}(L\text{-}Me^{n+})_i$ many different kind of topical-treatment products may be obtained, since the composition having the general formula $AO_x\text{-}(L\text{-}Me^{n+})_i$ may be suitably mixed with many different substances.

For example a product to be used for treating ulcers, and in particular bedsores, or decubitus ulcers, may be obtained.

In the following table 9 the percentage contents of a cream for topical use for treating ulcers are indicated.

TABLE 9

| Compound | Percentage [%] | Physical State | Adding phase |
|---|---|---|---|
| Water | 84.23 | Liquid | B |
| Isopropyl palmitate | 3.6 | Liquid | A |
| Petrolatum | 3 | pasty solid | A |
| Isohexadecane | 2 | Liquid | A |
| $AO_x\text{-}(L\text{-}Me^{n+})_i$ | 2 | Powder | C |
| Benzalkonium chloride 50% | 1.2 | Liquid | C |
| Bees wax(Cera Alba) | 1 | waxy solid | A |
| PPG-15 stearylether | 1 | Liquid | A |
| PEG-30 dipolyhydroxystearate | 1 | waxy solid | A |
| Methylparaben | 0.3 | Powder | B |
| Propylparaben | 0.2 | Powder | B |
| Citric acid | 0.2 | crystalline solid | B |
| Sodium dehydroacetate | 0.15 | Powder | B |
| Magnesium sulphate | 0.1 | crystalline solid | B |
| 2,4Bromonitropropandiol | 0.02 | crystalline solid | C |

The aforementioned compounds are weighed and dosed.

A turboemulsifier is heated up to a temperature of about 65°-70° C.

Phase "A": The compounds having the value "A" in the fourth column of the above table 2 are introduced into a turboemulsifier and mixed together. The turboemulsifier is heated up to a temperature of about 65°-70° C., so that the compounds in the turboemulsifier melt, and in the mean time the compounds are mixed.

Complete melting of the compounds has to be achieved, so that a better mixing can be obtained.

Phase "B": A further turboemulsifier is heated up to a temperature of about 75°-80° C. The compounds having the value "B" in the fourth column of the above table 2 are introduced in the further turboemulsifier, mixed together.

As the compounds in the turboemulsifier and in the further turboemulsifier reach the respective desired temperature values, both the turboemulsifier and the further turboemulsifier are closed, and operated so that the respective compounds in the turboemulsifier and in the further turboemulsifier could be mixed and homogenized.

Therefore, a vacuum pump, connected to the turboemulsifier is operated, and the compounds in the further turboemulsifier are poured into the turboemulsifier, i.e. compounds of phase "B" are poured in the compounds of phase "A".

The turboemulsifier is operated for few minutes so that the compounds of phase "A" and of phase "B" mix and homogenize together, the real mixing of the mixture can be checked and, if necessary, the turboemulsifier may be operated again.

After a desired mixing of the mixture has been obtained, the vacuum pump is operated, and the turboemulsifier is cooled down to a temperature of about 45° C.-50° C.

After such a temperature value has been reached, the vacuum pump is switched off and the compounds having the value "C" in the fourth column of the above table 9 are introduced into the turboemulsifier.

The turboemulsifier and the vacuum pump are both operated so that the compounds can be mixed and homogenized together, and the turboemulsifier is cooled during the homogenizing, down to a temperature of about 20°-30° C.

Such a temperature value is maintained for a certain time interval during which the compounds are continuously mixed.

After a certain time interval the product may be poured out form the turboemulsifier and analyzed. Analysis carried out have been demonstrated that the product is very stable over time and can be packed in subsequent packing operations and stocked without any risk of separations of the single compounds of the product.

The product obtained, called "Bactercline ulcer" hereinbelow for the sake of brevity, is an emulsion containing the composition having the general formula $AO_x\text{-}(L\text{-}Me^{n+})_i$ and additives, and other active principles, that can be used for obtaining topical-treatment products.

"Bactercline ulcer" is in a form of a cream that can be used for treating many skin ulcers, and in particular decubitus ulcers.

Owing to the very limited dimension of the composition having the general formula $AO_x\text{-}(L\text{-}Me^{n+})_i$; and the features thereof, an emulsion having very homogenous features is obtained.

As the compound having the general formula $AO_x\text{-}(L\text{-}Me^{n+})_i$ may for example used a compound containing titanium dioxide ($TiO_2$) as $AO_x$, silver perchlorate ($Ag^+ClO_4^-$) as $Me^+$ and a bifunctional ligand L suitable for bond both the titanium dioxide and the silver perchlorate.

In one embodiment 2 g of the compound having the general formula $AO_x\text{-}(L\text{-}Me^{n+})_i$ contain 1.998 g of $TiO_2$, 0.0084 g of $AgClO_4$, and 0.0062 g of 4-mercaptophenyl boronic acid as bifunctional ligand L.

A quaternary ammonium salt is also present, i.e. benzalkonium chloride that enhance the antibacterial, antimycotic, antimicrobial, antiviral properties of "Bactercline ulcer".

Similar "Bactercline ulcer" preparations may also be obtained using as bifunctional ligand L 6-mercaptonicotinic acid, and/or 11-mercaptoundecanoic acid, and/or mercaptosuccinic acid.

The "Bactercline ulcer" is a creamy, odourless emulsion, a water-in-oil-in water emulsion, having a white colour, with a density of about 0.995-1.005 g/cm³, and a viscosity of about 50,000-60,000 centipoise The creamy emulsion obtained may be spread on the skin, for example twice a day, owing to the physical features thereof the cream may be spread very easily, and forms on the skin of a user a protective layer, that is invisible and thus not unsightly, and that disinfect the skin allowing the ulcers to be treated.

The cutaneous tolerance of "Bactercline ulcer" has been tested on 50 adult volunteers, applying a 48-hours "Single patch test" under dermatological control.

The volunteers comprises 45 women and 5 men, aged between 18 and 65 years, average age 40 years, have normal skin and correspond to inclusion and non-inclusion criteria defined by DERMASCAN Group.

Inclusion criteria specified that the volunteers had given their informed written consent, had no previous experience of intolerance or allergic reactions to cosmetic products, belonged to phototype I to III.

Non inclusion criteria specified that the persons having the following features are not included as volunteers in the study: pregnant or nursing women, or women planning to be pregnant during the study, persons having cutaneous pathology (eczema, psoriasis, vitiligo, pytiriasis versicolor, acne, . . . ) on the zone of the experiment; volunteers currently taking or who stopped taking: antibiotics, anti-histamines, systemic anti-inflammatory drugs, or corticoids during the previous week, cough-suppressants or corticoids during the previous four weeks, retinoids, immunosuppressive drugs, anti-cancer drugs during the previous six months; volunteers who started, stopped, or changed hormonal treatment, including contraceptive pills, in the previous five week; volunteers whose skin has been exposed to the sun or to UV rays during the previous month; volunteers with very sensitive skin; volunteers having significant hair on the back, freckles, beauty spots, or a tattoo on the back; volunteers with serious diseases, volunteers using excessive quantity of alcohol or tobacco.

The product was applied on the scapular part of the back, using patch test of the type "Finn Chambers®" 8 mm (50 mm$^2$) of the occlusive type, using a dose of product for each patch test of 25 μl of the product in pure state.

Each patch was maintained on the skin of the volunteers for 48 hours.

Control patches without the product to be tested have been also applied to the volunteers.

After the 48-hours time interval the patches were removed from the skin, and after 30 min from the removal, a macroscopic skin examination was conducted with daylight lamps to evaluate the irritation grade of each one of the zones of the skin that had received the product.

Such evaluation was conducted comparing the real irritation of the skin with that obtained with the negative control patches.

If there was no local skin reaction at the 30 minutes reading after patch removal, the study was finished.

Nevertheless each volunteers was asked to confirm that there was non visible reactions the day after. If the volunteer had a visible reaction, he had to return and readings were taken until reversibility of the cutaneous reactions.

The scale in the following table 10 has been used to evaluate the degree of irritation:

TABLE 10

| Score | Quotation | Criteria description | |
|---|---|---|---|
| | | Erythema "E" | Oedema "O" |
| 0 | Absent | Normal aspect, no erythema | Normal aspect, no oedema |
| 0.5 | Doubtful | barely perceptible: slight pink coloration of one part of the tested area | Palpable, barely visible |
| 1 | Slight | slight pink coloration of the complete tested area, or rather visible on one part of the tested area | Palpable, visible |
| 2 | Obvious | Obvious erythema covering the whole tested area | Obvious oedema with or without papule(s) or vesicle(s) |
| 3 | Important | Severe erythema covering all the tested area or erythema diffusing outside the tested area | Severe oedema (diffusing outside the tested area) with or without papule(s) or vesicle(s |

A change in the skin structure, for example dryness (D), roughness (R1), thickness (T), reflectivity (R2), that could be linked to the nature of the product or one of its components was subjected to a clinical description and its intensity was graded according the following scale: 0.5=doubtful, 1=slight, 2=obvious, 3=important.

The analysis and the interpretation were carried out according to the results obtained in the experimental conditions at each reading.

The cutaneous tolerance of the cream has been evaluated calculating the "Mean Irritation Index" (MII) at each reading according to the formula MI=(Σ total cutaneous reactions score/(Total number of volunteers), a cutaneous reaction may be erythema and/or oedema, in case of presence of both erythema and oedema, the score of both erythema and oedema reactions were added.

The index MII obtained was used for arbitrarily classifying the product under study according to the following scale in table 11:

TABLE 11

| M.I.I. | Class |
|---|---|
| M.I.I. < 0.20 | non-irritating (NI) |
| 0.20 ≦ M.I.I. < 0.50 | slightly-irritating (SI) |
| 0.50 ≦ M.I.I. < 1 | moderately irritating (MI) |
| M.I.I. ≧ 1 | Irritating (I) |

M.I.I. was calculated for "Bactercline ulcer" either 30 min after the spreading of "Bactercline ulcer" on the skin of the volunteers, and 24-hours after the spreading.

Both the tests show a M.I.I. value for "Bactercline ulcer" of 0.00, therefore the cream produced is a non-irritating product.

Similar considerations may apply to "Bactercline acne" since the composition of the two products "Bactercline ulcer" and "Bactercline acne" is very similar, and also "Bactercline ulcer" contain more potentially aggressive compounds, therefore since "Bactercline ulcer" does not cause any irritation in the tested person, even more "Bactercline acne" would not have any irritation effect.

Under test conditions, it can be concluded that the product obtained according to the example 8 and tested under dermatological control and applied pure and locally under occlusive patch for 48 hours, to the skin of 50 adult volunteers, is classified as non-irritating at the 30 minute and 24-hours readings, according to the calculation of M.I.I.

The study has been carried out from Jul. 7, 2006 to Jul. 20, 2006 and from Jul. 7 2006 to Jul. 27, 2006 by the clinical Unit PROCOS, Warsaw, Poland.

The study was conducted according to the Good clinical Practice Guidelines from FDA (FR of Aug. 8, 1978 Part V—Decree Nr. 77N-0278), EEC (Directives Nr. 91/507 and III 3976/88 of Jul. 11, 1990) and to the ministry of health of the French Republic.

The study was conducted according to Standard Operating Procedures and the Protocol defined by the sponsor.

All the test events recorded during the study were reported.

Controls on data veracity and conformity to the protocol were conducted and confirmed by persons participating in the study.

Tests have been conducted according the standard procedure described in "European Standard EN14476, May 2002 (phase 2; step 1) edited by European Committee for standardization to evaluate the virucidal activity of "Bactercline ulcer".

A certain quota of a viral suspension is added to "Bactercline ulcer" both in "clean state", i.e. in a water solution containing 0.3 g/l of bovine albumin, and in "dirty state", i.e. in a water solution containing 3.0 g/l of bovine albumin and 0.3 ml of erythrocytes.

Suspension containing Adenovirus type 5 (ATCC VR5) and Poliovirus 1 Sabin strain having a titre, evaluated as $Log_{10}$ of $ID_{50}$, respectively of 5 5-8.15 for Adenovirus type 5 and of 1-8.20 for Poliovirus 1 Sabin strain and with different dilution rate comprised between 0 (undiluted suspension) and $10^{-4}$, were prepared, such suspensions were brought into contact with layers of HeLa cells at about 90%, these cells had been cultivated in MEM with 2% FBC, to evaluate the maximum viral concentration that does not cause morphological mutation in the cells.

Such a maximum concentration is $10^{-1}$. Therefore in tests undiluted suspensions of viruses have been used.

The viral suspensions and "Bactercline ulcer" were kept in contact at a temperature of about 20° C. for preset time intervals: 1 min, 10 min, 30 min, 60 min.

After each one of said time intervals a certain quantity of the mixing containing the viral suspension and "Bactercline ulcer" was removed, diluted using a 1:10 dilution ratio with a Minimal Essential Medium (MEM) and 2% of Fetal Calf Serum (FCS) for blocking the virucidal activity, and then analyzed to evaluate the virucidal activity of "Bactercline ulcer".

The virucidal activity was evaluated calculating the $ID_{50}$, i.e. the dilution of the viral suspension that causes cytopathic effects in 50% of the samples, as according to the "Spearman-Karber method".

The results of the tests are shown in the following table 12 and table 13, respectively for suspension of Poliovirus and Adenovirus 5.

TABLE 12

| Contact time | Viral titre "dirty" | Viral titre "clean" |
| --- | --- | --- |
| 60 min | −1.8 | −1.0 |
| 30 min | −3.0 | −2.0 |

TABLE 12-continued

| Contact time | Viral titre "dirty" | Viral titre "clean" |
| --- | --- | --- |
| 10 min | −4.0 | −3.0 |
| 1 min | −5.5 | −5.0 |

TABLE 13

| Contact time | Viral titre "dirty" | Viral titre "clean" |
| --- | --- | --- |
| 60 min | −1.0 | −1.0 |
| 30 min | −2.0 | −1.5 |
| 10 min | −3.5 | −2.5 |
| 1 min | −5.0 | −4.5 |

The values in second and third columns of the aforementioned tables 12, 13, indicate the negative logarithm of the 50% of the end-point.

The results obtained, show that a reduction higher than 4 $Log_{10}$ of the viral titre of the suspensions contacted with "Bactercline ulcer" was obtained for both the viral suspensions both in "clean" and in "dirty" states, for samples having a contact time interval of about 10 min.

The high virucidal activity of "Bactercline acne" was thus demonstrated.

The methodology of such tests has been verified for validating the results obtained. This validation was positive.

The invention claimed is:

1. A method for obtaining a topical-treatment product, said topical-treatment product being included in a group comprising: a topical-treatment product for treating acne diseases, a topical-treatment product for treating herpes diseases, a topical-treatment product for treating skin ulcers, a topical-treatment product for treating skin irritations, a topical-treatment product for treating skin inflammations, a topical-treatment product for treating skin abrasions, a topical-treatment product for treating skin excoriations, a cicatrizing topical-treatment product for cicatrizing the skin of a user, a burn topical-treatment product for treating burns on the skin of a user, a deodorizing topical-treatment product, a skincare topical-treatment product having antiviral, and/or antibacterial, and/or antimicrobial, and/or antimycotic properties, comprising providing a composition comprising nanoparticles and making said topical-treatment product that comprises said composition, wherein, in said composition, said nanoparticles have the general formula $AO_x$-$(L$-$Me^{n+})_i$, $AO_x$ being a metal or metalloid oxide in which x indicates the number of the Oxygen atom(s) (O) bonded to the metal (A) atom, $Me^{n+}$ being $Ag^+$, L being 4-mercaptophenylboronic acid, and i being the number of $(L$-$Me^{n+})$ groups bound to the metal oxide $AO_x$.

2. A method according to claim 1, wherein said skincare topical-treatment product comprises a day cream, and/or a night cream, and/or a cleansing cream, and/or a cleansing gel, and/or a moisturizing cream, and/or an anti-wrinkle cream, and/or a solar cream.

3. A method according to claim 1, wherein said topical-treatment product comprises at least a compound having antiviral, and/or antibacterial, and/or antimicrobial, and/or antimycotic properties.

4. A method according to claim 1, wherein said topical-treatment product comprises at least a compound effective in treating at least one of the following microbes: HSV-1 (Herpes Simplex Virus-1), Adenovirus, Poliovirus, Aviaria virus,

*Legionella pneumophila, Pseudomonas aeruginosa, Staphylococcus aureus, Enterococcus faecalis, Escherichia Coli, Salmonella enteridis* D1, *Listeria monocytogenes, Candida albicans, Aspergillus niger.*

5. A method according to claim 1, wherein said composition comprising nanoparticles having the general formula $AO_x\text{-}(L\text{-}Me^{n+})_i$ further comprises at least a quaternary ammonium salt for enhancing the properties of said topical-treatment product.

6. A method according to claim 5, wherein said composition comprising nanoparticles having the general formula $AO_x\text{-}(L\text{-}Me^{n+})_i$ further comprises at least a chloride ammonium salt.

7. A method according to claim 1, wherein said topical-treatment product comprises a cream product, and/or a gel product, and/or a powder product, and/or an emulsion product, and/or a suspension product, and/or a microspheres product, and/or a granular product, and/or a multiple emulsion product, and/or a water-in-oil-in water emulsion product.

8. A method according to claim 1, wherein said composition comprises at least an antibacterial component.

9. A method according to claim 1, wherein said composition further comprises at least an antiviral component.

10. A method according to claim 1, wherein said composition further comprises at least an antimycotic component.

11. A method according to claim 1, wherein said composition further comprises at least an antimicrobial component.

12. A method according to claim 1, wherein $AO_x$ is an oxide selected in a group comprising colloidal silica, titanium dioxide, zirconium dioxide, stannic dioxide, and zinc oxide.

13. A method according to claim 1, and further comprising a cationic surfactant bonded to said ligand L.

14. A method according to claim 13, wherein said cationic surfactant is chosen in a group comprising alkylammonium salts.

15. A method according to claim 1, wherein said topical-treatment product further comprises additives, and/or active principle, and/or excipients suitable for obtaining a dermatological product.

* * * * *